United States Patent
Gupta et al.

(10) Patent No.: US 9,741,001 B2
(45) Date of Patent: Aug. 22, 2017

(54) PREDICTIVE MEDICATION SAFETY

(71) Applicant: CareFusion 303, Inc., San Diego, CA (US)

(72) Inventors: Vikas Gupta, Naperville, IL (US); Scott Loebig, Carlsbad, CA (US); Federico Garibaldi, Encinitas, CA (US); Timothy W. Vanderveen, Poway, CA (US)

(73) Assignee: CAREFUSION 303, INC., San Diego, CA (US)

( * ) Notice: Subject to any disclaimer, the term of this patent is extended or adjusted under 35 U.S.C. 154(b) by 0 days.

(21) Appl. No.: 13/802,683

(22) Filed: Mar. 13, 2013

(65) Prior Publication Data

US 2013/0197931 A1  Aug. 1, 2013

(51) Int. Cl.
*G06Q 50/00* (2012.01)
*G06Q 10/06* (2012.01)
(Continued)

(52) U.S. Cl.
CPC ... *G06Q 10/06313* (2013.01); *G06F 19/3462* (2013.01); *G06F 19/3468* (2013.01); *G06Q 50/22* (2013.01); *G06F 19/326* (2013.01)

(58) Field of Classification Search
CPC .. G06F 19/30; G06F 19/3418; G06F 19/3481; G06F 19/3456; G06F 19/3406;
(Continued)

(56) References Cited

U.S. PATENT DOCUMENTS 2,141,006 A  12/1938  Marinsky
3,724,455 A   4/1973  Unger
(Continued)

FOREIGN PATENT DOCUMENTS

CA  2472098 A1  7/2003
CA  2554903 A1  4/2005
(Continued)

OTHER PUBLICATIONS

"'Smart' Infusion Pumps Join CPOE and Bar Coding as Important Ways to Prevent Medication Errors," ISMP—Medication Safety Alert, Feb. 7, 2002, 2 pgs., Institute for Safe Medication Practices.
(Continued)

*Primary Examiner* — Robert Sorey
(74) *Attorney, Agent, or Firm* — McDermott Will & Emery LLP

(57) ABSTRACT

Methods for facilitating safe use of a medical item are provided. In one aspect, a method includes receiving a first identifier for a medical entity located in an institution. The medical entity includes at least one of a patient, medical device, medical location, or medical item. The method also includes receiving a second identifier for a first course of action associated with the medical entity. The method further includes generating, based on a history of the medical entity and the first course of action associated with the medical entity, a second course of action for the medical entity, and providing a notification to a device indicating the second course of action. Systems and machine-readable media are also provided.

8 Claims, 5 Drawing Sheets

(51) Int. Cl.
  *G06Q 50/22* (2012.01)
  *G06F 19/00* (2011.01)

(58) Field of Classification Search
  CPC ....... G06F 19/345; G06Q 50/22–50/24; G06Q 10/06313
  See application file for complete search history.

(56) References Cited

U.S. PATENT DOCUMENTS

| | | |
|---|---|---|
| 3,831,006 A | 8/1974 | Chaffin, III et al. |
| 3,848,112 A | 11/1974 | Weichselbaum et al. |
| 3,872,448 A | 3/1975 | Mitchell, Jr. |
| 3,898,984 A | 8/1975 | Mandel et al. |
| 3,910,260 A | 10/1975 | Sarnoff et al. |
| 3,921,196 A | 11/1975 | Patterson |
| 3,970,996 A | 7/1976 | Yasaka et al. |
| 4,051,522 A | 9/1977 | Healy et al. |
| 4,135,241 A | 1/1979 | Stanis et al. |
| 4,164,320 A | 8/1979 | Irazoqui et al. |
| 4,216,462 A | 8/1980 | McGrath et al. |
| 4,237,344 A | 12/1980 | Moore |
| 4,315,309 A | 2/1982 | Coli |
| 4,321,461 A | 3/1982 | Walter, Jr. et al. |
| 4,360,125 A | 11/1982 | Martindale et al. |
| 4,373,527 A | 2/1983 | Fischell |
| 4,476,381 A | 10/1984 | Rubin |
| 4,604,847 A | 8/1986 | Moulding, Jr. et al. |
| 4,636,950 A | 1/1987 | Caswell et al. |
| 4,674,652 A | 6/1987 | Aten et al. |
| 4,676,776 A | 6/1987 | Howson |
| 4,688,026 A | 8/1987 | Scribner et al. |
| 4,695,954 A | 9/1987 | Rose et al. |
| 4,696,671 A | 9/1987 | Epstein et al. |
| 4,731,726 A | 3/1988 | Allen |
| 4,733,364 A | 3/1988 | Yamagata |
| 4,756,706 A | 7/1988 | Kerns et al. |
| 4,778,449 A | 10/1988 | Weber et al. |
| 4,785,969 A | 11/1988 | McLaughlin |
| 4,803,625 A | 2/1989 | Fu et al. |
| 4,810,243 A | 3/1989 | Howson |
| 4,828,545 A | 5/1989 | Epstein et al. |
| 4,831,562 A | 5/1989 | McIntosh et al. |
| 4,835,372 A | 5/1989 | Gombrich et al. |
| 4,839,806 A | 6/1989 | Goldfischer et al. |
| 4,847,764 A | 7/1989 | Halvorson |
| 4,850,009 A | 7/1989 | Zook et al. |
| 4,853,521 A | 8/1989 | Claeys et al. |
| 4,855,909 A | 8/1989 | Vincent et al. |
| 4,857,713 A | 8/1989 | Brown |
| 4,857,716 A | 8/1989 | Gombrich et al. |
| 4,865,584 A | 9/1989 | Epstein et al. |
| 4,882,575 A | 11/1989 | Kawahara |
| 4,899,839 A | 2/1990 | Dessertine et al. |
| 4,916,441 A | 4/1990 | Gombrich et al. |
| 4,918,604 A | 4/1990 | Baum |
| 4,925,444 A | 5/1990 | Orkin et al. |
| 4,942,544 A | 7/1990 | McIntosh et al. |
| 4,950,246 A | 8/1990 | Muller |
| 4,967,928 A | 11/1990 | Carter |
| 4,970,669 A | 11/1990 | McIntosh et al. |
| 4,978,335 A | 12/1990 | Arthur, III |
| 5,001,630 A | 3/1991 | Wiltfong |
| 5,006,699 A | 4/1991 | Felkener et al. |
| 5,036,462 A | 7/1991 | Kaufman et al. |
| 5,036,852 A | 8/1991 | Leishman |
| 5,072,383 A | 12/1991 | Brimm et al. |
| 5,077,666 A | 12/1991 | Brimm et al. |
| 5,078,683 A | 1/1992 | Sancoff et al. |
| 5,088,056 A | 2/1992 | McIntosh et al. |
| 5,088,981 A | 2/1992 | Howson et al. |
| 5,100,380 A | 3/1992 | Epstein et al. |
| 5,126,957 A | 6/1992 | Kaufman et al. |
| 5,142,484 A | 8/1992 | Kaufman et al. |
| 5,153,416 A | 10/1992 | Neeley |
| 5,153,827 A | 10/1992 | Coutre et al. |
| 5,164,575 A | 11/1992 | Neeley et al. |
| 5,166,498 A | 11/1992 | Neeley |
| 5,171,977 A | 12/1992 | Morrison |
| 5,181,910 A | 1/1993 | Scanlon |
| 5,207,642 A | 5/1993 | Orkin et al. |
| 5,235,507 A | 8/1993 | Sackler et al. |
| 5,256,157 A | 10/1993 | Samiotes et al. |
| 5,258,906 A | 11/1993 | Kroll et al. |
| 5,265,010 A | 11/1993 | Evans-Paganelli et al. |
| 5,267,174 A | 11/1993 | Kaufman et al. |
| 5,291,399 A | 3/1994 | Chaco |
| 5,292,029 A | 3/1994 | Pearson |
| 5,307,263 A | 4/1994 | Brown |
| 5,312,334 A | 5/1994 | Hara et al. |
| 5,314,243 A | 5/1994 | McDonald et al. |
| 5,315,505 A | 5/1994 | Pratt et al. |
| 5,317,506 A | 5/1994 | Coutre et al. |
| H1324 H | 6/1994 | Dalke et al. |
| 5,331,547 A | 7/1994 | Laszlo |
| 5,356,378 A | 10/1994 | Doan |
| 5,367,555 A | 11/1994 | Isoyama |
| 5,368,554 A | 11/1994 | Nazarian et al. |
| 5,371,692 A | 12/1994 | Draeger et al. |
| 5,374,813 A | 12/1994 | Shipp |
| 5,376,070 A | 12/1994 | Purvis et al. |
| 5,378,231 A | 1/1995 | Johnson et al. |
| 5,382,232 A | 1/1995 | Hague et al. |
| 5,390,238 A | 2/1995 | Kirk |
| 5,401,059 A | 3/1995 | Ferrario |
| 5,404,384 A | 4/1995 | Colburn et al. |
| 5,408,443 A | 4/1995 | Weinberger |
| 5,412,372 A | 5/1995 | Parkhurst et al. |
| 5,412,564 A | 5/1995 | Ecer |
| 5,416,695 A | 5/1995 | Stutman et al. |
| 5,456,691 A | 10/1995 | Snell |
| 5,460,605 A | 10/1995 | Tuttle et al. |
| 5,465,082 A | 11/1995 | Chaco |
| 5,472,614 A | 12/1995 | Rossi |
| 5,502,944 A | 4/1996 | Kraft et al. |
| 5,515,426 A | 5/1996 | Yacenda et al. |
| 5,522,798 A | 6/1996 | Johnson et al. |
| 5,533,079 A | 7/1996 | Colburn et al. |
| 5,536,084 A | 7/1996 | Curtis et al. |
| 5,538,006 A | 7/1996 | Heim et al. |
| 5,542,420 A | 8/1996 | Goldman et al. |
| 5,544,649 A | 8/1996 | David et al. |
| 5,544,661 A | 8/1996 | Davis et al. |
| 5,547,470 A | 8/1996 | Johnson et al. |
| 5,561,412 A | 10/1996 | Novak et al. |
| 5,562,232 A | 10/1996 | Pearson |
| 5,564,803 A | 10/1996 | McDonald et al. |
| 5,573,506 A | 11/1996 | Vasko |
| 5,582,593 A | 12/1996 | Hultman |
| 5,583,758 A * | 12/1996 | McIlroy et al. .................. 705/2 |
| 5,592,374 A | 1/1997 | Fellegara et al. |
| 5,594,786 A | 1/1997 | Chaco |
| 5,597,995 A | 1/1997 | Williams et al. |
| 5,601,445 A | 2/1997 | Schipper et al. |
| 5,622,429 A | 4/1997 | Heinze |
| 5,628,309 A | 5/1997 | Brown |
| 5,630,710 A | 5/1997 | Tune et al. |
| 5,633,910 A | 5/1997 | Cohen |
| 5,643,212 A | 7/1997 | Coutre et al. |
| 5,644,778 A | 7/1997 | Burks et al. |
| 5,645,531 A | 7/1997 | Thompson et al. |
| 5,651,775 A | 7/1997 | Walker et al. |
| 5,655,118 A | 8/1997 | Heindel et al. |
| 5,657,236 A | 8/1997 | Conkright |
| 5,658,250 A | 8/1997 | Blomquist et al. |
| 5,672,154 A | 9/1997 | Sillen et al. |
| 5,681,285 A | 10/1997 | Ford et al. |
| 5,683,367 A | 11/1997 | Jordan et al. |
| 5,685,844 A | 11/1997 | Marttila |
| 5,689,229 A | 11/1997 | Chaco et al. |
| 5,692,640 A | 12/1997 | Caulfield et al. |
| 5,699,038 A | 12/1997 | Ulrich et al. |
| 5,700,998 A | 12/1997 | Palti |
| 5,703,786 A | 12/1997 | Conkright |
| 5,704,352 A | 1/1998 | Tremblay et al. |

(56) References Cited

U.S. PATENT DOCUMENTS

| | | |
|---|---|---|
| 5,710,551 A | 1/1998 | Ridgeway |
| 5,712,913 A | 1/1998 | Chaum |
| 5,713,856 A | 2/1998 | Eggers |
| 5,721,913 A | 2/1998 | Ackroff et al. |
| 5,733,259 A | 3/1998 | Valcke et al. |
| 5,737,539 A | 4/1998 | Edelson |
| 5,738,102 A | 4/1998 | Lemelson |
| 5,752,235 A | 5/1998 | Kehr et al. |
| 5,758,095 A | 5/1998 | Albaum et al. |
| 5,758,096 A | 5/1998 | Barsky et al. |
| 5,760,704 A | 6/1998 | Barton et al. |
| 5,764,034 A | 6/1998 | Bowman et al. |
| 5,772,585 A | 6/1998 | Lavin et al. |
| 5,774,865 A | 6/1998 | Glynn |
| 5,781,442 A | 7/1998 | Engleson et al. |
| 5,790,409 A | 8/1998 | Fedor et al. |
| 5,795,327 A | 8/1998 | Wilson et al. |
| 5,803,906 A | 9/1998 | Pratt et al. |
| 5,807,321 A | 9/1998 | Stoker et al. |
| 5,807,336 A | 9/1998 | Russo et al. |
| 5,819,229 A | 10/1998 | Boppe |
| 5,822,418 A | 10/1998 | Yacenda et al. |
| 5,822,544 A | 10/1998 | Chaco et al. |
| 5,832,488 A | 11/1998 | Eberhardt |
| 5,833,599 A | 11/1998 | Schrier et al. |
| 5,842,173 A | 11/1998 | Strum et al. |
| 5,842,976 A | 12/1998 | Williamson |
| 5,845,253 A | 12/1998 | Rensimer et al. |
| 5,845,254 A | 12/1998 | Lockwood et al. |
| 5,845,255 A | 12/1998 | Mayaud |
| 5,845,264 A | 12/1998 | Nelhaus |
| 5,848,593 A | 12/1998 | McGrady et al. |
| 5,850,344 A | 12/1998 | Conkright |
| 5,852,408 A | 12/1998 | Christiansen et al. |
| 5,855,550 A | 1/1999 | Lai et al. |
| 5,867,821 A | 2/1999 | Ballantyne et al. |
| 5,871,465 A | 2/1999 | Vasko |
| 5,883,806 A | 3/1999 | Meador et al. |
| 5,885,245 A | 3/1999 | Lynch et al. |
| 5,894,273 A | 4/1999 | Meador et al. |
| 5,895,371 A | 4/1999 | Levitas et al. |
| 5,899,998 A | 5/1999 | McGauley et al. |
| 5,903,211 A | 5/1999 | Flego et al. |
| 5,905,653 A | 5/1999 | Higham et al. |
| 5,907,490 A | 5/1999 | Oliver |
| 5,911,132 A | 6/1999 | Sloane |
| 5,911,687 A | 6/1999 | Sato et al. |
| 5,912,818 A | 6/1999 | McGrady |
| 5,920,054 A | 7/1999 | Uber, III |
| 5,920,263 A | 7/1999 | Huttenhoff et al. |
| 5,928,329 A | 7/1999 | Clark et al. |
| 5,930,145 A | 7/1999 | Yuyama et al. |
| 5,935,099 A | 8/1999 | Peterson et al. |
| 5,941,710 A | 8/1999 | Lampotang et al. |
| 5,942,986 A | 8/1999 | Shabot et al. |
| 5,950,630 A | 9/1999 | Portwood et al. |
| 5,950,632 A | 9/1999 | Reber et al. |
| 5,953,099 A | 9/1999 | Walach |
| 5,954,641 A | 9/1999 | Kehr et al. |
| 5,957,885 A | 9/1999 | Bollish et al. |
| 5,961,036 A | 10/1999 | Michael et al. |
| 5,961,446 A | 10/1999 | Beller et al. |
| 5,971,593 A | 10/1999 | McGrady |
| 5,995,077 A | 11/1999 | Wilcox et al. |
| 6,000,828 A | 12/1999 | Leet |
| 6,003,006 A | 12/1999 | Colella |
| 6,009,333 A | 12/1999 | Chaco |
| 6,021,392 A | 2/2000 | Lester et al. |
| 6,024,699 A | 2/2000 | Surwit et al. |
| 6,032,155 A | 2/2000 | de la Huerga |
| 6,039,251 A | 3/2000 | Holowko et al. |
| 6,047,203 A | 4/2000 | Sackner et al. |
| 6,048,087 A | 4/2000 | Laurent et al. |
| 6,053,887 A | 4/2000 | Levitas et al. |
| 6,063,026 A | 5/2000 | Schauss et al. |
| 6,082,776 A | 7/2000 | Feinberg |
| 6,112,182 A | 8/2000 | Akers et al. |
| RE36,871 E | 9/2000 | Epstein et al. |
| 6,134,582 A | 10/2000 | Kennedy |
| 6,135,949 A | 10/2000 | Russo et al. |
| 6,202,923 B1 | 3/2001 | Boyer et al. |
| 6,228,057 B1 | 5/2001 | Vasko |
| 6,241,704 B1 | 6/2001 | Peterson et al. |
| 6,269,340 B1 | 7/2001 | Ford et al. |
| 6,282,441 B1 | 8/2001 | Raymond et al. |
| 6,290,681 B1 | 9/2001 | Brown |
| 6,292,698 B1 | 9/2001 | Duffin et al. |
| 6,302,844 B1 | 10/2001 | Walker et al. |
| 6,312,378 B1 | 11/2001 | Bardy |
| 6,314,556 B1 * | 11/2001 | DeBusk et al. ............... 717/107 |
| 6,319,200 B1 | 11/2001 | Lai et al. |
| 6,322,502 B1 | 11/2001 | Schoenberg et al. |
| 6,338,007 B1 | 1/2002 | Broadfield et al. |
| 6,339,732 B1 | 1/2002 | Phoon et al. |
| 6,406,426 B1 | 6/2002 | Reuss et al. |
| 6,409,684 B1 | 6/2002 | Wilk |
| 6,421,650 B1 | 7/2002 | Goetz et al. |
| 6,493,747 B2 | 12/2002 | Simmon et al. |
| 6,519,569 B1 | 2/2003 | White et al. |
| 6,529,892 B1 | 3/2003 | Lambert |
| 6,540,672 B1 | 4/2003 | Simonsen et al. |
| 6,558,352 B1 | 5/2003 | Hogan |
| 6,581,606 B2 | 6/2003 | Kutzko et al. |
| 6,671,563 B1 | 12/2003 | Engelson et al. |
| 6,745,764 B2 | 6/2004 | Hickle |
| 6,757,898 B1 | 6/2004 | Ilsen et al. |
| 6,785,589 B2 | 8/2004 | Eggenberger et al. |
| 6,796,956 B2 | 9/2004 | Hartlaub et al. |
| 6,799,149 B2 | 9/2004 | Hartlaub |
| 6,847,861 B2 | 1/2005 | Lunak et al. |
| 6,856,247 B1 | 2/2005 | Wallace |
| 6,993,402 B2 | 1/2006 | Klass et al. |
| 7,034,691 B1 | 4/2006 | Rapaport et al. |
| 7,054,844 B2 | 5/2006 | Fletcher et al. |
| 7,096,072 B2 | 8/2006 | Engleson et al. |
| 7,215,991 B2 | 5/2007 | Besson et al. |
| 7,229,430 B2 | 6/2007 | Hickle et al. |
| 7,230,529 B2 | 6/2007 | Ketcherside, Jr. et al. |
| 7,256,708 B2 | 8/2007 | Rosenfeld et al. |
| 7,263,492 B1 | 8/2007 | Suresh et al. |
| 7,379,885 B1 | 5/2008 | Zakim |
| 7,384,420 B2 | 6/2008 | Dycus et al. |
| 7,398,183 B2 | 7/2008 | Holland et al. |
| 7,421,709 B2 | 9/2008 | Watson et al. |
| 7,433,853 B2 | 10/2008 | Brockway et al. |
| 7,471,994 B2 | 12/2008 | Ford et al. |
| 7,526,769 B2 | 4/2009 | Watts et al. |
| 7,587,415 B2 | 9/2009 | Gaurav et al. |
| 7,612,679 B1 | 11/2009 | Fackler et al. |
| 7,693,697 B2 | 4/2010 | Westenskow et al. |
| 7,769,601 B1 | 8/2010 | Bleser et al. |
| 7,771,385 B2 | 8/2010 | Eggers et al. |
| 7,771,386 B2 | 8/2010 | Eggers et al. |
| 7,787,946 B2 | 8/2010 | Stahmann et al. |
| 7,796,045 B2 | 9/2010 | Spear et al. |
| 7,835,927 B2 | 11/2010 | Schlotterbeck et al. |
| 7,847,970 B1 | 12/2010 | McGrady |
| 7,860,583 B2 | 12/2010 | Condurso et al. |
| 7,962,544 B2 | 6/2011 | Torok et al. |
| 7,970,550 B2 | 6/2011 | Arakelyan et al. |
| 8,005,688 B2 | 8/2011 | Coffman et al. |
| 8,024,200 B2 | 9/2011 | Jennings et al. |
| 8,160,895 B2 | 4/2012 | Schmitt et al. |
| 8,197,437 B2 | 6/2012 | Kalafut et al. |
| 8,291,337 B2 | 10/2012 | Gannin et al. |
| 8,340,792 B2 | 12/2012 | Condurso et al. |
| 8,689,008 B2 | 4/2014 | Rangadass et al. |
| 2001/0037083 A1 | 11/2001 | Hartlaub et al. |
| 2001/0044731 A1 | 11/2001 | Coffman et al. |
| 2002/0010679 A1 | 1/2002 | Felsher |
| 2002/0016568 A1 | 2/2002 | Lebel et al. |
| 2002/0016923 A1 | 2/2002 | Knaus et al. |
| 2002/0022973 A1 | 2/2002 | Sun et al. |
| 2002/0026223 A1 | 2/2002 | Riff et al. |

(56) References Cited

U.S. PATENT DOCUMENTS

| | | |
|---|---|---|
| 2002/0033548 A1 | 3/2002 | Brodkin et al. |
| 2002/0035484 A1 | 3/2002 | McCormick |
| 2002/0038392 A1 | 3/2002 | De La Huerga |
| 2002/0042636 A1 | 4/2002 | Koshiol et al. |
| 2002/0046346 A1 | 4/2002 | Evans |
| 2002/0077849 A1 | 6/2002 | Baruch et al. |
| 2002/0087114 A1 | 7/2002 | Hartlaub |
| 2002/0116509 A1 | 8/2002 | De La Huerga |
| 2002/0120350 A1 | 8/2002 | Klass et al. |
| 2002/0169636 A1 | 11/2002 | Eggers et al. |
| 2002/0198624 A1 | 12/2002 | Greenwald et al. |
| 2003/0009244 A1 | 1/2003 | Engleson et al. |
| 2003/0036683 A1 | 2/2003 | Kehr et al. |
| 2003/0045858 A1 | 3/2003 | Struys et al. |
| 2003/0051737 A1 | 3/2003 | Hickle et al. |
| 2003/0063524 A1 | 4/2003 | Niemiec et al. |
| 2003/0069481 A1 | 4/2003 | Hervy et al. |
| 2003/0105389 A1 | 6/2003 | Noonan et al. |
| 2003/0105555 A1 | 6/2003 | Lunak et al. |
| 2003/0106553 A1 | 6/2003 | Vanderveen |
| 2003/0114836 A1 | 6/2003 | Estes et al. |
| 2003/0121517 A1 | 7/2003 | McFarland |
| 2003/0129578 A1 | 7/2003 | Mault |
| 2003/0135087 A1 | 7/2003 | Hickle et al. |
| 2003/0135388 A1 | 7/2003 | Martucci et al. |
| 2003/0139701 A1 | 7/2003 | White et al. |
| 2003/0140928 A1 | 7/2003 | Bui et al. |
| 2003/0140929 A1 | 7/2003 | Wilkes et al. |
| 2003/0149599 A1 | 8/2003 | Goodall et al. |
| 2003/0156143 A1 | 8/2003 | Westenskow et al. |
| 2003/0158746 A1 | 8/2003 | Forrester |
| 2003/0163223 A1 | 8/2003 | Blomquist |
| 2003/0205897 A1 | 11/2003 | Kaufman |
| 2003/0236683 A1 | 12/2003 | Henderson et al. |
| 2004/0068229 A1 | 4/2004 | Jansen et al. |
| 2004/0073329 A1 | 4/2004 | Engleson et al. |
| 2004/0107118 A1 | 6/2004 | Harnsberger et al. |
| 2004/0122702 A1 | 6/2004 | Sabol et al. |
| 2004/0122705 A1 | 6/2004 | Sabol et al. |
| 2004/0122719 A1 | 6/2004 | Sabol et al. |
| 2004/0122790 A1 | 6/2004 | Walker et al. |
| 2004/0128162 A1 | 7/2004 | Schlotterbeck et al. |
| 2004/0152622 A1 | 8/2004 | Keith et al. |
| 2004/0167465 A1 | 8/2004 | Mihai et al. |
| 2004/0167804 A1 | 8/2004 | Simpson et al. |
| 2004/0172283 A1 | 9/2004 | Vanderveen et al. |
| 2004/0172300 A1* | 9/2004 | Mihai .................. A61B 5/0002 705/2 |
| 2004/0172302 A1 | 9/2004 | Martucci et al. |
| 2004/0176297 A1 | 9/2004 | Cheung et al. |
| 2004/0188998 A1 | 9/2004 | Henthorn |
| 2004/0193325 A1 | 9/2004 | Bonderud et al. |
| 2004/0193446 A1 | 9/2004 | Mayer et al. |
| 2004/0260478 A1 | 12/2004 | Schwamm |
| 2005/0010166 A1 | 1/2005 | Hickle |
| 2005/0020996 A1 | 1/2005 | Hartlaub et al. |
| 2005/0021297 A1 | 1/2005 | Hartlaub |
| 2005/0033606 A1 | 2/2005 | Miller |
| 2005/0049179 A1 | 3/2005 | Davidson et al. |
| 2005/0055242 A1 | 3/2005 | Bello et al. |
| 2005/0088296 A1 | 4/2005 | Lee |
| 2005/0096941 A1 | 5/2005 | Tong |
| 2005/0097566 A1 | 5/2005 | Watts et al. |
| 2005/0107914 A1 | 5/2005 | Engleson et al. |
| 2005/0108057 A1 | 5/2005 | Cohen et al. |
| 2005/0113945 A1 | 5/2005 | Engleson et al. |
| 2005/0119788 A1 | 6/2005 | Engleson et al. |
| 2005/0144043 A1 | 6/2005 | Holland et al. |
| 2005/0145010 A1 | 7/2005 | Vanderveen et al. |
| 2005/0148890 A1 | 7/2005 | Hastings |
| 2005/0171815 A1 | 8/2005 | Vanderveen |
| 2005/0224083 A1 | 10/2005 | Crass et al. |
| 2005/0278194 A1 | 12/2005 | Holland et al. |
| 2006/0026205 A1 | 2/2006 | Butterfield |
| 2006/0047538 A1 | 3/2006 | Condurso et al. |
| 2006/0053036 A1 | 3/2006 | Coffman et al. |
| 2006/0101072 A1 | 5/2006 | Busche et al. |
| 2006/0122481 A1 | 6/2006 | Sievenpiper et al. |
| 2006/0190302 A1 | 8/2006 | Eggers et al. |
| 2006/0200369 A1 | 9/2006 | Batch et al. |
| 2006/0206356 A1 | 9/2006 | Vanderveen |
| 2006/0217628 A1 | 9/2006 | Huiku |
| 2006/0218015 A1 | 9/2006 | Walker et al. |
| 2006/0229551 A1 | 10/2006 | Martinez et al. |
| 2006/0249423 A1 | 11/2006 | Reijonen |
| 2006/0271401 A1 | 11/2006 | Lassetter et al. |
| 2006/0287890 A1 | 12/2006 | Stead et al. |
| 2007/0015972 A1 | 1/2007 | Wang et al. |
| 2007/0043767 A1 | 2/2007 | Osborne et al. |
| 2007/0061266 A1 | 3/2007 | Moore et al. |
| 2007/0061393 A1 | 3/2007 | Moore |
| 2007/0083389 A1* | 4/2007 | Dyer et al. .................. 705/2 |
| 2007/0106457 A1 | 5/2007 | Rosenberg |
| 2007/0106753 A1 | 5/2007 | Moore |
| 2007/0106754 A1 | 5/2007 | Moore |
| 2007/0156860 A1 | 7/2007 | Nedelcu et al. |
| 2007/0168301 A1 | 7/2007 | Eisner et al. |
| 2007/0208454 A1 | 9/2007 | Forrester et al. |
| 2007/0210157 A1 | 9/2007 | Miller |
| 2007/0286466 A1 | 12/2007 | Heffernan et al. |
| 2007/0293843 A1 | 12/2007 | Ireland et al. |
| 2008/0015549 A1 | 1/2008 | Maughan |
| 2008/0025230 A1 | 1/2008 | Patel et al. |
| 2008/0034323 A1 | 2/2008 | Blomquist |
| 2008/0040151 A1 | 2/2008 | Moore |
| 2008/0046292 A1 | 2/2008 | Myers et al. |
| 2008/0141272 A1 | 6/2008 | Borgendale et al. |
| 2008/0162254 A1 | 7/2008 | Herger et al. |
| 2008/0164998 A1* | 7/2008 | Scherpbier et al. ...... 340/539.13 |
| 2008/0169045 A1 | 7/2008 | Tribble et al. |
| 2008/0195246 A1 | 8/2008 | Tribble et al. |
| 2008/0272138 A1 | 11/2008 | Ross et al. |
| 2008/0317672 A1 | 12/2008 | Viertio-Oja |
| 2009/0012812 A1 | 1/2009 | Rausch et al. |
| 2009/0012813 A1 | 1/2009 | Berzansky |
| 2009/0099867 A1 | 4/2009 | Newman |
| 2009/0112333 A1 | 4/2009 | Sahai |
| 2009/0150484 A1 | 6/2009 | Roberts |
| 2009/0210252 A1 | 8/2009 | Silver |
| 2009/0240651 A1 | 9/2009 | Fletcher et al. |
| 2009/0306585 A1 | 12/2009 | Pang et al. |
| 2009/0306944 A1 | 12/2009 | Willmann et al. |
| 2009/0319623 A1 | 12/2009 | Srinivasan et al. |
| 2010/0037067 A1 | 2/2010 | Rangadass et al. |
| 2010/0094653 A1 | 4/2010 | Tribble et al. |
| 2010/0121654 A1 | 5/2010 | Portnoy et al. |
| 2010/0161113 A1 | 6/2010 | Tribble et al. |
| 2010/0169120 A1 | 7/2010 | Herbst et al. |
| 2010/0169771 A1 | 7/2010 | Pelegrin et al. |
| 2010/0174552 A1 | 7/2010 | Hawkes et al. |
| 2010/0174553 A1 | 7/2010 | Kaufman et al. |
| 2010/0179825 A1 | 7/2010 | Hanov et al. |
| 2010/0241453 A1 | 9/2010 | Malec |
| 2010/0241456 A1 | 9/2010 | Miller et al. |
| 2010/0271218 A1 | 10/2010 | Hoag et al. |
| 2010/0280840 A1 | 11/2010 | Fukushi et al. |
| 2010/0323397 A1 | 12/2010 | Reavy et al. |
| 2011/0015941 A1 | 1/2011 | Backhaus |
| 2011/0046975 A1 | 2/2011 | Hoffman |
| 2011/0060758 A1 | 3/2011 | Schlotterbeck et al. |
| 2011/0119612 A1 | 5/2011 | Gannon et al. |
| 2011/0179405 A1 | 7/2011 | Dicks et al. |
| 2011/0202495 A1 | 8/2011 | Gawlick |
| 2011/0282691 A1 | 11/2011 | Coffman et al. |
| 2011/0288882 A1* | 11/2011 | Halow .................. 705/2 |
| 2011/0313787 A1 | 12/2011 | Rangadass et al. |
| 2012/0011253 A1 | 1/2012 | Friedman et al. |
| 2012/0016215 A1 | 1/2012 | Condurso et al. |
| 2012/0041775 A1 | 2/2012 | Cosentino et al. |
| 2012/0053533 A1 | 3/2012 | Butterfield et al. |
| 2012/0075061 A1 | 3/2012 | Barnes |
| 2012/0136673 A1 | 5/2012 | Presley et al. |
| 2012/0173264 A1 | 7/2012 | Brush et al. |
| 2012/0182939 A1 | 7/2012 | Rajan et al. |

(56) References Cited

U.S. PATENT DOCUMENTS

| | | |
|---|---|---|
| 2012/0185267 A1 | 7/2012 | Kamen et al. |
| 2012/0191052 A1 | 7/2012 | Rao |
| 2012/0239824 A1 | 9/2012 | Nguyen et al. |
| 2012/0247480 A1 | 10/2012 | Varga |
| 2012/0253835 A1 | 10/2012 | Tracy et al. |
| 2012/0265549 A1 | 10/2012 | Virolainen |
| 2013/0018356 A1 | 1/2013 | Prince et al. |
| 2013/0085771 A1 | 4/2013 | Ghanbari et al. |
| 2013/0096444 A1 | 4/2013 | Condurso et al. |
| 2013/0197927 A1 | 8/2013 | Vanderveen et al. |
| 2013/0197928 A1 | 8/2013 | Vanderveen et al. |
| 2013/0197929 A1 | 8/2013 | Vanderveen et al. |
| 2013/0197930 A1 | 8/2013 | Garibaldi et al. |
| 2013/0197931 A1 | 8/2013 | Gupta et al. |
| 2013/0204433 A1 | 8/2013 | Gupta et al. |
| 2013/0204637 A1 | 8/2013 | Vanderveen et al. |
| 2013/0262138 A1 | 10/2013 | Jaskela et al. |
| 2014/0028464 A1 | 1/2014 | Garibaldi |
| 2014/0100868 A1 | 4/2014 | Condurso et al. |
| 2014/0278466 A1 | 9/2014 | Simmons et al. |
| 2014/0297313 A1 | 10/2014 | Condurso et al. |
| 2014/0350950 A1 | 11/2014 | Jaskela et al. |
| 2015/0250948 A1 | 9/2015 | Gupta et al. |
| 2016/0000997 A1 | 1/2016 | Batch et al. |

FOREIGN PATENT DOCUMENTS

| | | |
|---|---|---|
| CN | 1759398 A | 4/2006 |
| CN | 101116077 A | 1/2008 |
| CN | 101146055 A | 3/2008 |
| CN | 201110955 Y | 9/2008 |
| CN | 101890193 A | 11/2010 |
| CN | 102068725 A | 5/2011 |
| CN | 102688532 A | 9/2012 |
| DE | 4023785 | 1/1992 |
| EP | 0192786 | 9/1986 |
| EP | 0384155 | 8/1990 |
| EP | 0595474 | 5/1994 |
| EP | 0649316 | 4/1995 |
| EP | 0652528 | 5/1995 |
| EP | 0784283 | 7/1997 |
| EP | 0921488 | 6/1999 |
| EP | 1003121 | 5/2000 |
| EP | 1018347 | 7/2000 |
| EP | 1237113 | 9/2002 |
| GB | 2141006 | 12/1984 |
| JP | 62114562 | 5/1987 |
| JP | 5168708 | 7/1993 |
| JP | 11-505352 | 5/1999 |
| JP | 2002-520718 | 7/2002 |
| JP | 2003085283 A | 3/2003 |
| JP | 2004287616 A | 10/2004 |
| JP | 2006155070 A | 6/2006 |
| KR | 1020070045611 A | 5/2007 |
| KR | 1020080013129 A | 2/2008 |
| KR | 100847397 B1 | 7/2008 |
| KR | 1020100125972 A | 12/2010 |
| KR | 1020110070824 A | 6/2011 |
| KR | 1020120076615 A | 7/2012 |
| KR | 1020120076635 A | 7/2012 |
| NZ | 522631 A | 7/2004 |
| WO | WO93/22735 | 11/1993 |
| WO | WO94/05344 | 3/1994 |
| WO | WO94/08647 | 4/1994 |
| WO | WO94/13250 | 6/1994 |
| WO | WO95/23378 | 8/1995 |
| WO | WO96/20745 | 7/1996 |
| WO | WO-9620745 A1 | 7/1996 |
| WO | WO96/25214 | 8/1996 |
| WO | WO-9625214 A1 | 8/1996 |
| WO | WO96/36923 | 11/1996 |
| WO | WO97/04712 | 2/1997 |
| WO | WO98/13783 | 4/1998 |
| WO | WO98/28676 | 7/1998 |
| WO | WO99/09505 | 2/1999 |
| WO | WO99/10829 | 3/1999 |
| WO | WO99/10830 | 3/1999 |
| WO | WO99/35588 | 7/1999 |
| WO | WO99/44167 | 9/1999 |
| WO | WO99/45490 | 9/1999 |
| WO | WO99/46718 | 9/1999 |
| WO | WO99/67732 | 12/1999 |
| WO | WO00/03344 | 1/2000 |
| WO | WO00/04521 | 1/2000 |
| WO | WO00/18449 | 4/2000 |
| WO | WO00/32088 | 6/2000 |
| WO | WO00/32098 | 6/2000 |
| WO | WO01/86506 | 11/2001 |
| WO | WO01/88828 | 11/2001 |
| WO | WO02/36044 | 5/2002 |
| WO | WO02/069099 | 9/2002 |
| WO | WO03/038566 | 5/2003 |
| WO | WO03/053503 | 7/2003 |
| WO | WO03/092769 | 11/2003 |
| WO | WO03/094091 | 11/2003 |
| WO | WO2004/060443 | 7/2004 |
| WO | WO2004/061745 | 7/2004 |
| WO | WO-2010124016 A1 | 10/2010 |
| WO | WO-2010124328 A1 | 11/2010 |
| WO | WO-2012095829 A2 | 7/2012 |

OTHER PUBLICATIONS

"General-Purpose Infusion Pumps," Evaluation—Health Devices, Oct. 2002, pp. 353-387, vol. 31(10), ECRI Institute.
"Infusion Pump Technology," Health Devices, Apr.-May 1998, pp. 150-170, vol. 27(4-5), ECRI Institute.
"Infusion Pumps, General-Purpose," Healthcare Product Comparison System, 2007, pp. 1-54, ECRI Institute.
"Infusion Pumps, Large-Volume," Healthcare Product Comparison System, 2010, pp. 1-51, ECRI Institute.
Anonymous, Guardrails® Safety Software—Medley TM Medication Safety System, Alaris Medical Systems XP-00234431; 2002 Alaris Medical Systems Inc. Nov. 2002, SSM @2159C.
Baldauf-Sobez et al., "How Siemens' Computerized Physician Order Entry Helps Prevent the Human Error," Electromedica, vol. 71, No. 1, 2003, pp. 2-10.
Calabrese, et al., "Medication administration errors in adult patients in the ICU," Intensive Care Med, 2001, pp. 1592-1598, vol. 27, Springer-Verlag.
Eskew, James et al., Using Innovative Technologies to Set New Safety Standards for the Infusion of Intravenous Medications, Hospital Pharmacy, vol. 37, No. 11, pp. 1179-1189, 2002, Facts and Comparisons.
Kohn, et al., "To Err is Human—Building a Safer Health System," National Academy Press, 2002, pp. i-287, National Academy of Sciences.
Lesar, "Recommendations for Reducing Medication Errors," Medscape Pharmacists, posted Jul. 24, 2000, 10 pgs, vol. 1(2), Medscape Pharmacists, <http://www.medscape.com>.
Meier, "Hospital Products Get Seal of Approval at a Price," The New York Times, Apr. 23, 2002, 5 pgs.
Shabot, et al., "Wireless clinical alerts for critical medication, laboratory and physiologic data," System Sciences 2000. Proceedings of the 33rd Annual Conference on Jan. 4-7, 2000, Piscataway, NJ, IEEE, Jan. 4, 2000.
Williams, et al., "Reducing the Risk of User Error with Infusion Pumps," Professional Nurse—Safe Practice—Infusion Devices, Mar. 2000, pp. 382-384, vol. 15(6).
Yokoi, "Prevention of Errors in Injection/Drip Infusion—No excuse for ignorance!—Essential Points of Accident Prevention, IV Infusion Pump, Syringe-pump Accident Prevention," JIN Special, Igaku Shoin K.K., Dec. 1, 2001, pp. 109-120, No. 70.
U.S. Appl. No. 13/901,501, filed May 23, 2013.
International Search Report and Written Opinion of the International Searching Authority dated Sep. 5, 2014, for PCT application PCT/US2014/037577.
International Search Reports and Written Opinion of the International Searching Authority dated Jun. 18, 2014 and Jun. 19, 2014 for

(56) References Cited

OTHER PUBLICATIONS

PCT applications PCT/US2014/022830, PCT/US2014/022835 and PCT/US2014/022837. Office Action issued in U.S. Appl. No. 13/802,433 dated Aug. 25, 2014.
Non-Final Office Action dated Oct. 14, 2014, issued in U.S. Appl. No. 11/326,145, and Non-Final Office Action dated Oct. 24, 2014, issued in U.S. Appl. No. 13/559,537.
International Search Reports and Written Opinions of the International Searching Authority dated Jun. 19, 2014 and Jun. 24, 2014 for PCT Application Nos. PCT/US2014/022840 and PCT/US2014/022532.
U.S. Appl. No. 90/009,912, filed Aug. 12, 2013, Schlotterbeck et al.
U.S. Appl. No. 90/011,697, filed Aug. 12, 2013, Schlotterbeck et al.
Queensland Health. Use of returned or unused dispensed medicines, Jan. 5, 2005, Queensland Government. pp. 1-2.
International Search Report and Written Opinion, Application No. PCT/US2014/022840, Jun. 19, 2014, 13 pgs.
International Search Report and Written Opinion, Application No. PCT/US2014/022832, Jun. 24, 2014, 12 pgs.
Extended European Search Report for Application No. 14779655.1, dated Jul. 14, 2016, 8 pages.
Extended European Search Report for Application No. 14780320.9, dated Jul. 1, 2016, 7 pages.
Evans, R. S. et al., "Enhanced notification of infusion pump programming errors", Studies in health technology and informatics, Jan. 1, 2010, pp. 734-738, XP055305644, Netherlands DOI: 10.3233/978-1-60750-588-4-734 Retrieved from the Internet: URL:http://booksonline.iospress.nl/Extern/EnterMedLine.aspx?ISSN=0926-9630&Volume=160&SPage=734 [retrieved on Sep. 26, 2016].
Extended European Search Report and Written Opinion for Application No. 14772937.0, dated Oct. 10, 2016, 9 pages.
Extended European Search Report and Written Opinion for Application No. 14779139.6, dated Nov. 7, 2016, 7 pages.
Extended European Search Report for Application No. 14801713.0, dated Jan. 16, 2017, 8 pages.
Canadian Office Action for Application No. 2512991, dated Mar. 2, 2017, 4 pages.
Extended European Search Report for Application No. 14801726.2, dated Jan. 5, 2017, 8 pages.
Extended European Search Report for Application No. 14775918.7, dated Sep. 13, 2016, 10 pages.
Chinese Office Action for Application No. 201480015147.6, dated Mar. 10, 2017, 10 pages excluding translation.
Canadian Office Action for Application No. 2551903, dated Mar. 28, 2017, 7 pages.
European Office Action for Application No. 12756903.6, dated Apr. 19, 2017, 5 pages.
Office Action for United Arab Emirates Application No. UAE/P/0962/2013, dated Apr. 17, 2017, 18 pages.

\* cited by examiner

PREDICTIVE MEDICATION SAFETY

BACKGROUND

Field

The present disclosure generally relates to medical devices, and particularly to configuring medical devices to reduce error.

Description of the Related Art

Medication errors, that is, errors that occur in the ordering, dispensing, and administration of medications, regardless of whether those errors cause injury or not, are a significant consideration in the delivery of healthcare in the institutional setting. Additionally, adverse drug events (ADE), which are defined as injuries involving a drug that require medical intervention and are a subset of medication errors, represent some of the most serious medication errors are responsible for a number of patient injuries and death.

Healthcare facilities continually search for ways to reduce the occurrence and severity of medication errors. Various systems and methods are commonly used to reduce the frequency of occurrence and severity of preventable adverse drug events (PADE) and other medication errors. In the administration of medication, focus is typically directed to the following five "rights" or factors: the right patient, the right drug, the right route, the right amount, and the right time. Systems and methods seeking to reduce ADEs and PADEs should take these five rights into consideration.

Delivery, verification, and control of medication in an institutional setting have traditionally been areas where errors can occur. In a typical healthcare facility, a physician enters an order for a medication for a particular patient. This order may be handled either as a simple prescription slip, or it may be entered into an automated system, such as a physician order entry (POE) system. The prescription slip or the electronic prescription from the POE system is routed to the pharmacy, where the order is filled. Typically, pharmacies check the physician order against possible allergies of the patient and for possible drug interactions in the case where two or more drugs are prescribed, and also check for contraindications. Depending on the healthcare facility, the medication may be identified and gathered within the pharmacy and placed into a transport carrier for transport to a nurse station. Once at the nurse station, the prescriptions are again checked against the medications that have been identified for delivery to ensure that no errors have occurred. Each of these steps or workflows is typically captured as event data in a hospital information system. The event data is not, however, used to adjust future workflows involving medical items. For example, a medical item from a dispensing cabinet may have an associated warning related to how commonly the medical item is wasted. This information is not, however, used to adjust future workflows from reducing waste of the medical item.

SUMMARY

According to one embodiment of the present disclosure, a method for facilitating safe use of a medical item is provided. The method includes receiving a first identifier for a medical entity located in an institution. The medical entity includes at least one of a patient, medical device, medical location, or medical item. The method also includes receiving a second identifier for a first course of action associated with the medical entity. The method further includes generating, based on a history of the medical entity and the first course of action associated with the medical entity, a second course of action for the medical entity, and providing a notification to a device indicating the second course of action.

According to another embodiment of the present disclosure, a monitoring system for facilitating safe use of a medical item is provided. The system includes a memory that includes a history of a medical entity located in an institution. The medical entity includes at least one of a patient, medical device, medical location, or medical item. The system also includes a processor. The processor is configured to receive a first identifier for the medical entity and a second identifier for a first course of action associated with the medical entity, and generate, based on a history of the medical entity and the first course of action associated with the medical entity, a second course of action for the medical entity. The processor is also configured to provide a notification to a device indicating the second course of action.

According to a further embodiment of the present disclosure, a machine-readable storage medium that includes machine-readable instructions for causing a processor to execute a method for facilitating safe use of a medical item is provided. The method includes receiving a first identifier for a medical entity located in an institution. The medical entity includes at least one of a patient, medical device, medical location, or medical item. The method also includes receiving a second identifier for a first course of action associated with the medical entity. The method further includes generating, based on a history of the medical entity and the first course of action associated with the medical entity, a second course of action for the medical entity, and providing a notification to a device indicating the second course of action.

According to yet a further embodiment of the present disclosure, a method for instructing a caregiver is provided. The method includes receiving a first identity of a caregiver at an institution and a proposed course of action for a medical entity, and generating, based on a history of the caregiver within the institution, a modified course of action. The method also includes providing a notification of the modified course of action to the caregiver.

It is understood that other configurations of the subject technology will become readily apparent to those skilled in the art from the following detailed description, wherein various configurations of the subject technology are shown and described by way of illustration. As will be realized, the subject technology is capable of other and different configurations and its several details are capable of modification in various other respects, all without departing from the scope of the subject technology. Accordingly, the drawings and detailed description are to be regarded as illustrative in nature and not as restrictive.

BRIEF DESCRIPTION OF THE DRAWINGS

The accompanying drawings, which are included to provide further understanding and are incorporated in and constitute a part of this specification, illustrate disclosed embodiments and together with the description serve to explain the principles of the disclosed embodiments. In the drawings.

DETAILED DESCRIPTION

In the following detailed description, numerous specific details are set forth to provide a full understanding of the present disclosure. It will be apparent, however, to one ordinarily skilled in the art that the embodiments of the present disclosure may be practiced without some of these specific details. In other instances, well-known structures and techniques have not been shown in detail so as not to obscure the disclosure.

Each of the steps of a workflow related to a medical entity, such as a patient, medical device, medical location, or medical item, can be captured as event data in a hospital information system. The event data can be, for example, historical data related to the medical entity. The disclosed system leverages the event data for the medical entity to determine, for example, whether to suggest an alternative workflow for the medical entity. For instance, event information for a medication from a dispensing cabinet may be evaluated by the disclosed system to determine a percentage of times the medication is wasted. The disclosed system may then send a notification to a caregiver attempting to dispense the medication regarding the potential wastage, and may further restrict the caregiver from dispensing the medication until additional verification steps are taken. Similar notifications and workflow suggestions can be suggested for improving a health level of a patient, expediting dispensing of a medical item, indicating an incidence rate of illness in a medical location, or a recommending an increase of an order being placed for medical items based on a recent change in demand for the medical item. The notifications and other workflow suggestions can be specific to the caregiver specific when, for example, an abnormal utilization pattern for a medical item is specific to the caregiver.

Several examples will now be presented regarding how the disclosed system can assist a caregiver in facilitating a safe interaction with a medical entity. As one example, a notification can be sent if a certain medication is continuously used to address a certain pathology when it is shown that the patient length of stay is not improved over time using that medication. As another example, a specific nurse can be alerted to check on order information if the nurse is historically hitting safe or therapeutic limits on doses too often. As yet another example, a specific caregiver can be informed that the caregiver's level of drug waste is high on average. As a further example, a pharmacist can be informed that a certain medication may be required statim (e.g., "stat" or urgently) because the medication has historically taken a long time to be delivered to a patient.

Figure 1:
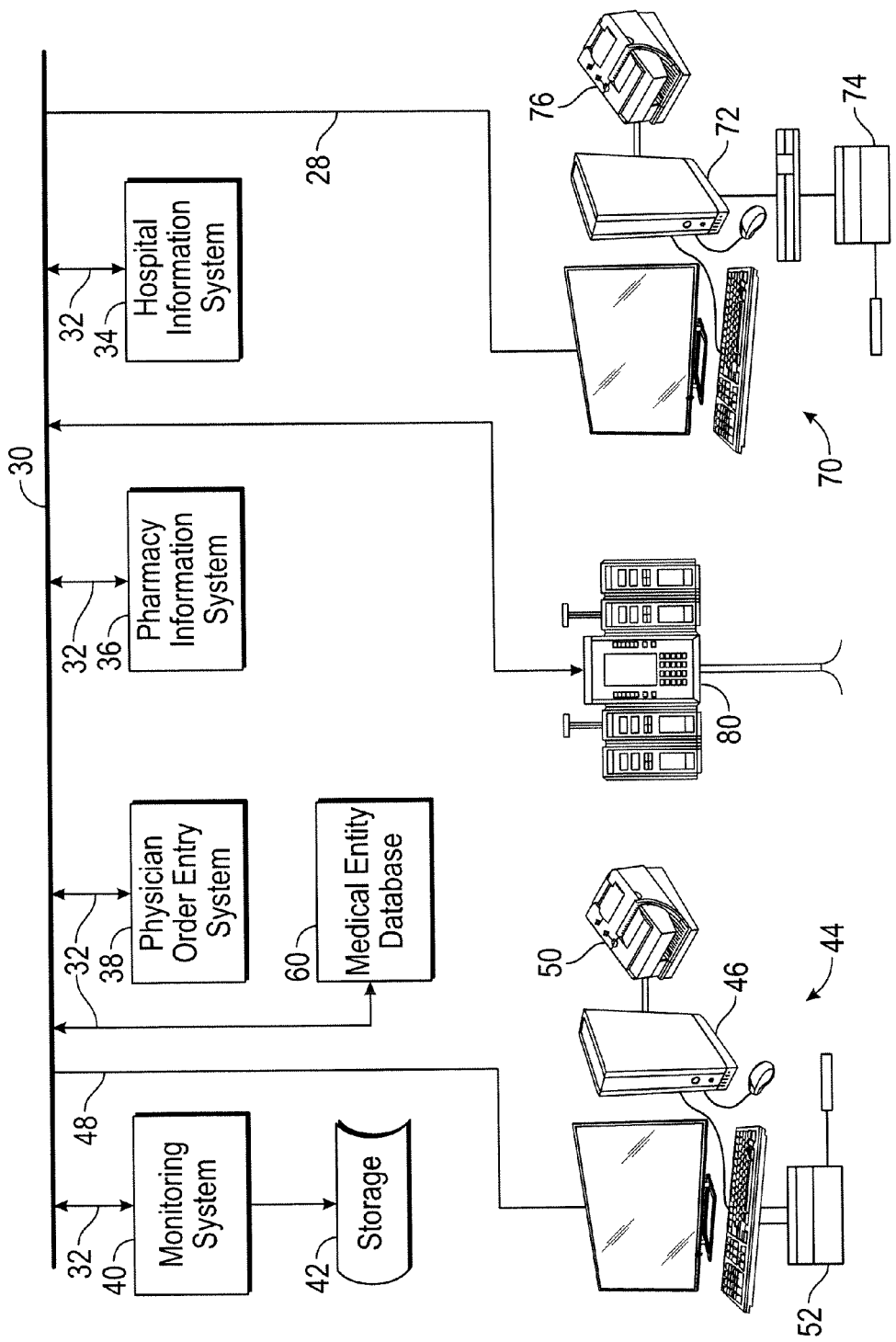
FIG. 1 illustrates a block diagram of a system for facilitating safe use of a medical item.

Referring now to the drawings, FIG. 1 provides an example illustration of an integrated healthcare facility-wide information and care management system 28 in accordance with certain aspects of the present disclosure. Various subsystems of a healthcare facility's information management system are connected together by way of a facility communication system 30. The communication system 30 may include, for example, any one or more of a personal area network (PAN), a local area network (LAN), a campus area network (CAN), a metropolitan area network (MAN), a wide area network (WAN), a broadband network (BBN), the Internet, and the like. Further, the communication system 30 can include, but is not limited to, any one or more of the following network topologies, including a bus network, a star network, a ring network, a mesh network, a star-bus network, tree or hierarchical network, and the like. As shown in FIG. 1, the communication system 30 connects through various interfaces 32 to a healthcare facility information system 34, a pharmacy information system 36, a physician order entry system 38, a medical entity database 60, and a monitoring system 40.

The facility communication system 30 is not meant to be taken in a limited sense. Such a facility communication system 30 may encompass an entire healthcare facility or may be located only in a small area of the healthcare facility. It may also include a communication system in a healthcare facility other than a hospital and may have application to an alternate care facility, such as a patient's home. Additionally, the word caregiver is intended to be used in its broadest sense and is meant to include nurses, physicians, health care specialists, and others who provide care to patients.

The monitoring system 40 in accordance with an aspect of the present disclosure may be, for example, a server or other computer having sufficient memory 42 and processing capability to connect with the communication system 30 and determine a change in workflow for a healthcare process. The monitoring system 40 includes operational software or other instructions for carrying out various aspects of the present disclosure, as will be discussed more fully below, enabling communications with other hardware or networks, and data input and output and report generation and printing, among other functions. While the monitoring system 40 is shown as a separate piece of equipment, it will be understood that the monitoring system 40 and the associated memory 42 may also be incorporated into another element, such as the medical device 80.

The communication system 30 may comprise, for example, a wired or wireless Ethernet (IEEE 522.3) utilizing transmitters and receivers positioned throughout the healthcare facility and/or attached to various computers, clinical devices and other equipment used in the facility. In such a wireless system, the signals transmitted and received by the system could be radio frequency (RF), infrared (IR), or other means capable of carrying information in a wireless manner between devices having appropriate transmitters or receivers may be used. It will be immediately understood by those skilled in the art that such a system may be identical to the system set forth in FIG. 1, with the exception that no wires are required to interconnect the various aspects of the system.

In a typical healthcare facility, patient rooms, wards, or areas are typically situated in groups located near a nurse station 44, where the caregivers assigned to care for the patients in the particular area carry out the administrative functions of their duties. Typically, these functions include updating and monitoring the patients' charts, preparation of and administering medication orders, and monitoring and recording any other information deemed necessary by the facility for tracking. There is also usually a room located adjacent the nurse station that is dedicated to storage and/or the preparation of medications to be delivered to patients. This room may contain inventories of commonly used oral, IM, or IV medications. The room may also be used to formulate the contents of infusion bags in accordance with prescribed treatment regimens.

The nurse station 44 will typically include a terminal or computer system 46 connected either directly or through an interface 48 to the communication system 30, allowing users at the nurse station to enter and retrieve patient data or information from other systems, such as the healthcare facility information system 34, the pharmacy information system 36, the physician order entry system 38, or other systems used in the facility. It should be understood that not all users will be provided with access rights to each system. For example, physicians may be able to access the physician order entry system 38 from the nurse station system 44 to enter, edit, or track medication orders, but a caregiver may only be able to view such orders. Moreover, while the present disclosure is described with reference to the computer system 46 being located at a nurse station 44, the computer system 46 may also be a satellite system that is located anywhere in the care-giving facility where it is convenient or efficient to do so. Such a satellite computer system may be operably connected to the communication system 30 using either a wired or wireless network connection. A printer 50 may also be connected to the nurse station computer system 46 for printing reports, bar codes, labels, or other materials, and a bar code reader 52 may be provided for reading bar codes on medication labels, reports, or other items having bar coded labels provided for identification.

In a different embodiment where radio frequency identification (RFID) tags are used with medications, patients, equipment, or in other ways, the nurse station 44 may also include an interrogator or RFID reader (not shown) for use with the RFID tags.

In accordance with aspects of the present disclosure, a medical entity database 60 stores information related to medical entities, such as patients, medical devices, medical locations, and medical items. Various types of information may be stored in the memory of the medical entity database 60, including medical item history and course of action information (e.g., orders, history of use, caregivers associated with the item, etc.). Databases can also be stored in the database 60 that contain information about drug interactions and possible contraindications and/or side-effects of medications, and established guidelines for the administration of various medications. For example, the guidelines may include institutionally-established guidelines or limits on drug administration parameters, such as dosage, frequency of administration, and other delivery related information such as, for example, appropriate flow rates and infusion durations for programming infusion pumps. Additionally, the guidelines may encompass guidelines for providing drug administration appropriate to a particular patient or to treatment areas having different sets of delivery parameters for similar medications, such as medication administration directed to geriatric, pediatric, and oncology patients. Guidelines may also be included that are directed to particular therapy regimens, such as chemotherapy regimens or regimens for treating chronic infection or pain. The term database as used herein will be understood by those skilled in the art to be used as is commonly understood. That is, the term database refers to a collection of values or information organized, formatted, and stored in such a manner as to be capable of being retrieved and analyzed using an appropriate program contained in software or other form.

The medications guidelines database 60 may be stored on a device, such as a server. The healthcare facility may also or alternatively have the medical entity database 60 centrally located in the memory 42 of the monitoring system 40. The medical entity database 60 includes medication information, medical item history, and course of action information, and/or databases or libraries, including institutionally generated guidelines for the delivery of medication to a patient, as well as drug interaction information or information concerning possible drug side-effects. The medications guidelines database 60 may also have a storage capability and technology for interfacing with a computer system or network so that information may be communicated between the medications guidelines database 60 and other devices, such as computers, medication administration devices, clinical devices such as vital signs monitoring devices and the like. A general concept embodied in the medications guidelines database 60 is to provide safe medication guidelines for dispensing, administering, or otherwise providing medication a patient using, for example, a medical device 80 such as an infusion pump.

In accordance with aspects of the present disclosure, the monitoring system 40 is configured to obtain medical entity information from the medical entity database 60. The medical entity database 60 is configured to obtain device information from the medical device 80, previous medical item history and course of action information (e.g., orders, history of use, caregivers associated with the item, etc.) from physician order entry system 38, the pharmacy information system 36, and the healthcare facility information system 34. Information may be retrieved information from the medical device 80 prior to actual medication administration. Monitoring system 40 can determine, based on a history of a medical entity and a current course of action for the medical entity, whether an alternative course of action should be taken for the medical entity. If the determination indicates an alternative course of action should be taken, then the monitoring system 40 is configured to transmit a notification to a relevant caregiver or device indicating the alternative course of action. The monitoring system 40 may also restrict or otherwise inhibit the current course of action from being taken (e.g., by locking a device).

For example, physician order system 38 may indicate that a certain medication is to be provided to a patient, and the pharmacy information system 36 may indicate how often the medication has been dispensed to the patient in the past. Based on this information, the monitoring system 40 may determine that dispensing the medication to the patient is harmful according to certain medical guidelines (e.g., from medical entity database 60). The monitoring system may then prevent a medical device 80 from dispensing the medication by locking the medical device 80 and possibly requiring a manual override of the lock in order to dispense the medication to the patient.

As another example, the pharmacy information system 36 may indicate that an order for 30 doses of a medication is to be placed, and the healthcare facility information system 34 may indicate that an incidence of an illness (e.g., with reference to patient laboratory data) that is treated by the medication has increased sharply in the past 24 hours. Based on the order and incidence information, the monitoring can send a notification to the pharmacy information system 36 to increase the number of doses being ordered, and may provide a suggested amount based on the incidence information.

As yet a further example, the healthcare facility information system 34 may include a caregiver's history regarding medication and medical device usage, and the medical entity database 60 may indicate an appropriate amount of a medication the caregiver has given in the past. The monitoring system 40 may determine that the amount of the medication the caregiver has given in the past has been inadequate, and send a notification to the medical device 80 or another device of the caregiver indicating that the medication amount provided by the caregiver should be increased.

While specific examples of a monitoring system 40 are set forth herein, it will be understood that the monitoring system 40 is meant to include any device that carries out the basic concept of the disclosure. That is, a device that receives an identification of a medical entity, such as a patient, medical device, medical location, or medical item, and an identification of a course of action associated with the medical entity, and has a processor that generates, based on a history of the medical entity and the course of action associated with the medical entity, a second (e.g., alternative) course of action for the medical entity, and provides a notification to a device (e.g., device of a caregiver, medical device 80, physician order entry system 38, pharmacy information system 36, healthcare facility information system 34) indicating the second course of action.

One particular mode of operation of the present disclosure will now be described. A patient entering a healthcare facility is provided with a wrist band, necklace, ankle band, or other band, chain, or device designed to remain affixed to or embedded in the patient during the patient's entire stay in the healthcare facility (the "patient ID"). The patient ID is designed to remain affixed in a manner so that the patient can be identified even if unconscious or otherwise unresponsive. The patient ID is used to identify specific patient data, such as the patient's name and other information that the facility has determined is important, such as age, allergies, or other vital information. The patient identifying device may comprise a bar code, written information, or an electronic information storage device, such as an RF transponder (e.g., RFID tag), that contains the information, or other device affixed to the patient. In the case where the patient-specification information may also include the patient's medication administration record (MAR). This would allow for consistent documentation and also checks against drug interaction in the medical entity database 60.

Such RFID tags, barcodes, and other technologies useful in identification, may be applied to others and to other things in providing healthcare to patients. For example, physicians, nurses, and other caregivers, as well as others who have access to patients and facilities, may also have an RFID tag that can be read anywhere in the healthcare facility. The medical fluid containers may contain RFID tags having information about the contents of the container as well as the patient for whom they have been prepared, the pharmacist who prepared them, and the physician who prescribed them. The infusion pumps and other healthcare instruments and devices may have RFID tags useful for inventory control. Even though the instruments may be connected to the healthcare facility communication system 30, RFID tags can be useful for manual inventory purposes as well as for other purposes. Their low cost makes them attractive as a backup support system.

After the patient is admitted and situated in a bed within the facility, the patient is typically evaluated by a physician and a course of treatment is prescribed. The physician prescribes a course of treatment by preparing an order that may request a series of laboratory tests or the administration of a particular medication to the patient. In some cases, the physician prepares the order by filling in a form or writing the order on a slip of paper to be entered into the healthcare facility system for providing care. In other cases, the physician may enter the medication order directly into a physician order entry system 38 or may instruct a nurse or other care-giving professional to do so. In yet another case, the physician may use the Internet to forward and enter a prescription for the patient into the pharmacy system. Depending on the arrangement at the healthcare facility, the physician's order or prescription may directly reach a website for the pharmacy information system 36 or may go to a website for the healthcare facility where it may then be routed to the pharmacy information system 36. In certain aspects, the monitoring system 40 may review the prescribed course of treatment for the patient and the history of prescriptions by the physician or other physicians, and propose an alternative treatment for the patient to the physician for review.

Pharmacy information systems 36 may enable a safer physician medication order process. The pharmacy information system 36 may provide the physician with a list of available drugs from which the physician may select. The pharmacy information system 36 may contain a drug library having the list of available drugs but may also contain and present to the physician the drug names associated with recommended dosages and dose limits that have been established or adopted by the healthcare facility. In such a case where the physician need only select items from the computer screen rather than having to manually type in drug names and drug administration numbers (such as infusion rates, times, etc.) associated with administration of the medication, a more accurate medication process should result.

If the order is for administration of a particular medication regimen, the order will be transmitted to the facility's pharmacy information system 36. The pharmacy reviews the order. In certain aspects, the monitoring system 40 may, for example, review the particular medication regimen for the patient and the history of medication regimens for the patient or similar patients, and then propose an medication regiment for the patient to the pharmacist (or physician) for review.

The pharmacy prepares the medication according to the requirements of the physician. Typically, the pharmacy packages the medication in a container, and a copy of the order, or at a minimum the patient's name, the drug name, and the appropriate treatment parameters are represented on a label or other device that is affixed to the drug container. This information may be represented by a bar code, or it may be stored in a smart label, such as a label having an embedded computer, or in a passive device such as an RFID tag discussed above.

Once the order has been prepared, the order is sent to the nurse station 44 for matching with the appropriate patient. Alternatively, if the medication is for a commonly or routinely prescribed medication, the medication may be included in an inventory of medications that is stored in a secure cabinet adjacent the nurse station 44. In such a case, the nurse station 44 will receive a list of orders from the pharmacy information system 36 that may be drawn from the inventory adjacent the nurse station 44. The caregiver will enter a unique identifier at the cabinet to gain access in accordance with standard practice. The caregiver or other professional assigned the task of gathering medications will then match the orders received from the pharmacy information system 60 to the medications stored in the inventory and pull those medications that are to be delivered to specific patients. These procedures are carried out whether the medication to be delivered is an oral medication or a medication that is to be delivered intramuscularly or through an infusion. In certain aspects, the monitoring system 40 may review the medication orders to determine, for example, whether the caregiver has a particularly high level of waste for the medication order being dispensed. If such a determination is made, the monitoring system 40 may send a notification to the nurse station 44 for the caregiver to view. The notification can state, for example, the caregiver's recorded history of waste and either remind the caregiver to be careful in dispensing the medication order, or propose an alternative workflow to dispensing the medication order.

In certain circumstances, a pharmacy dispenses a vial of a medication (a "multidose vial") that includes more than the specific dose of the medication required for a patient. one advisory that we should give the nurse is exactly how to prepare the medication. A nurse or other caregiver may then be tasked calculating an appropriate dose of the medication for the patient based on the total amount of medication included in the vial. For example, a physician may order that a 65 kg patient receive a 40 unit/kg bolus dose, and the administration of the medication should be at a rate not to exceed 400 units/minute. The vial of the medication contains 1000 units/mL. The nurse must manually calculate the total dose of the vial, namely, that the vial contains 2600 units of the medication. The nurse must then determine that this is 2.6 mL of the 1000 units/mL, and then calculate the dose injection for a minimum time of 6.5 minutes. The disclosed monitoring system 40 may advantageously provide this information to the nurse so that the nurse, such as a notification to remove 2.6 mL of the 1000 units/mL medication and administer at 0.4 Ml/min, and further provide the syringe label complete with patient, drug, dose and bar code to the nurse.

When the prescribed time for delivery of the medication or medications arrives, the medications are carried to the patient's area and administered to the patient by the caregiver. In the case of drugs to be delivered via infusion, the caregiver hangs the infusion bag and prepares the infusion line, attaches the bag to an infusion pump 80, and sets up the infusion pump to deliver the medication by programming the pump with values for various parameters that are used by the pump to control delivery of the medication to the patient. When the medication delivery parameters are entered into the pump, the pump communicates the entered parameters to the medical entity database 60. In certain aspects, the monitoring system 40 may, for example, review the medication delivery parameters and a history of previous medication delivery parameters entered into the infusion pump 80 to deliver the medication or similar medications, and determine that alternative medication delivery parameters should be used. If such a determination is made, the monitoring system 40 may send a notification to the infusion pump 80 for the caregiver to view. The notification can propose, for example, alternative medication delivery parameters and a reason for proposing the alternative medication delivery parameters. If the alternative medication delivery parameters for the infusion pump 80 are accepted, or alternatively manually overridden, the monitoring system 40 can send a signal to the infusion pump 80 to begin infusion of the medication.

Figure 2:
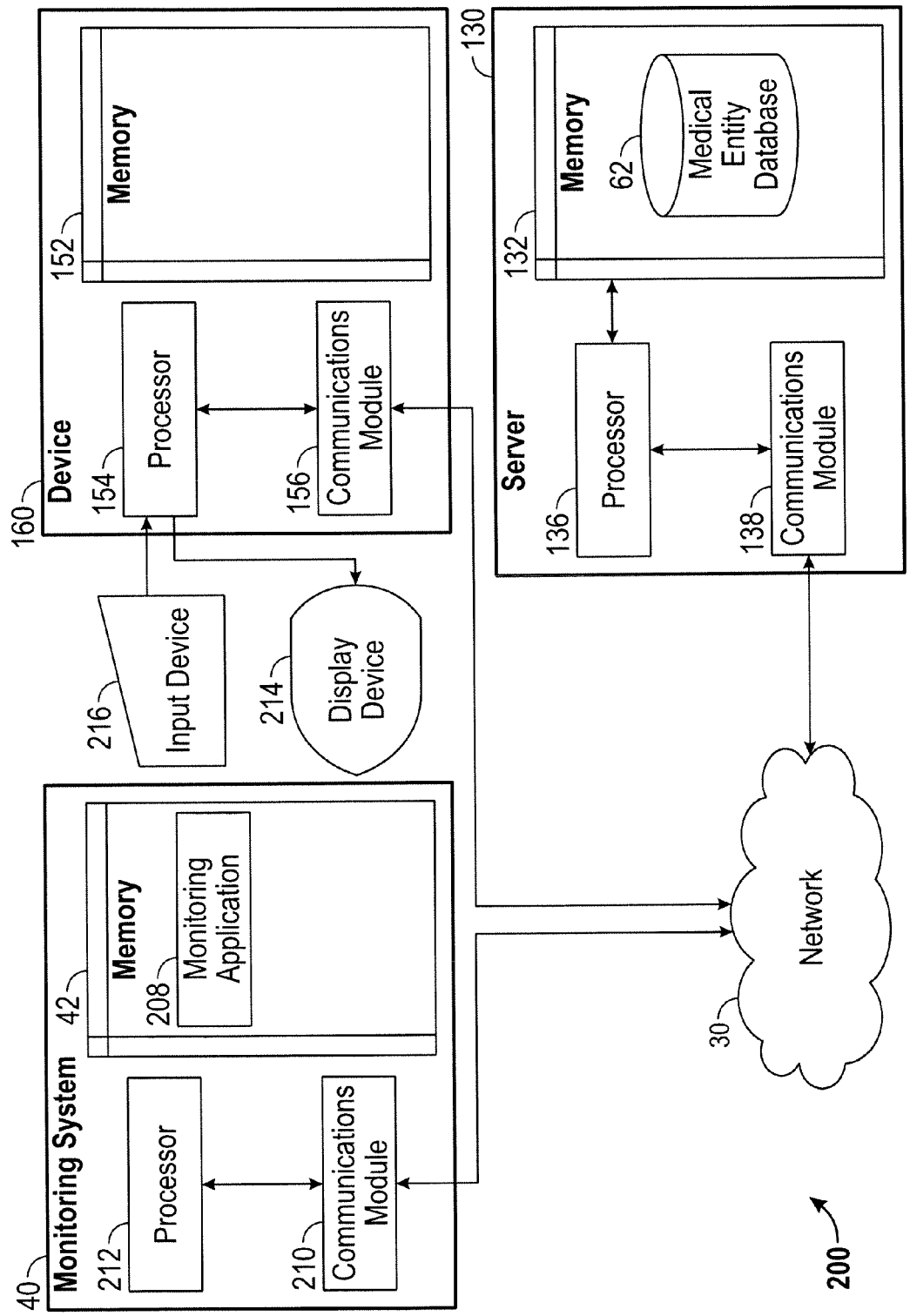
FIG. 2 is a block diagram illustrating the monitoring system and server from the architecture of FIG. 1 according to certain aspects of the disclosure.

FIG. 2 is a block diagram 200 illustrating an example monitoring system 40 and server 130 from the architecture of FIG. 1 according to certain aspects of the disclosure. The control system 40, a device 160 (e.g., such as medical device 80), and the server 130 are connected over the network 30 via respective communications modules 210, 156, and 138. The communications modules 210, 156, and 138 are configured to interface with the network 30 to send and receive information, such as data, requests, responses, and commands to other devices on the network. The communications modules 210, 156, and 138 can be, for example, modems or Ethernet cards and communicate over a wired or wireless connection.

The monitoring system 40 includes a processor 212, the communications module 210, and a memory 42 that includes a monitoring application 208. The monitoring application 208 includes instructions for the processor 212 to obtain, from the processor 136 of the server 130, information from the medical entity database 62 over the network 30 using respective communications modules 210 and 138 of the monitoring system 40 and the server 130. The information received from the medical entity database 62 includes identification information for a medical entity, courses of action associated with the medical entity, and a history of the medical entity. The medical entity can be, for example, a patient, medical device 80, medical location (e.g., hospital or area within a hospital, such as an Intensive Care Unit), or medical item such as a medication or medical. For example, identification information for a medical entity can be a name or unique identifier for a patient. A course of action associated with a medical entity can be providing a prescribed amount of medication to a patient. A history of a medical entity can be a listing of medications administered using a medical device 80.

The processor 212 of the monitoring system 40 is configured to execute instructions, such as instructions physically coded into the processor 212, instructions received from software in memory 42, or a combination of both. For example, the processor 212 of the monitoring system 40 executes instructions from the monitoring application 208 to receive a first identifier for a medical entity located in an institution and a second identifier for a first course of action associated with the medical entity. The first and second identifiers can be received from the medical entity database 62 over the network 30. The processor 212 of the monitoring system is also configured to generate, based on a history of the medical entity and the first course of action associated with the medical entity, a second course of action for the medical entity, and provide a notification to the device 160 indicating the second course of action. The second course of action can be, for example, an alternative to the first course of action selected in order to promote a safe or efficient interaction with the medical entity. The device 160 can be, for example, a caregiver's mobile device, a medical device 80 at or near a patient's bedside, a display at a nurse station 44, or a display of the healthcare facility information system 34, pharmacy information system 36, physician order entry system 38, or monitoring system 40. The notification can include a message indicating a purpose for indicating the second course of action. For example, a notification can be displayed using display device 214 on a caregiver's mobile device 160 indicating a prescribed amount of medication for the patient is too high based on the patient's physiological history relative to administration of the medication, and further indicate an alternative amount of medication that is appropriate to the patient based on the patient's physiological history relative to administration of the medication. The caregiver may then be asked to confirm or override the alternative amount using an input device 216 of the mobile device 160.

The first identifier, the second identifier, or the history of the medical entity can be received from an external data system (e.g., server 130) in a native message format of the external data system, and the processor 212 of the monitoring system 40 can be configured to convert the first identifier, the second identifier, or the history of the medical entity into an internal messaging format configured for use with the monitoring system 40. The processor 212 can be configured to perform the conversion according to the system and method of converting messages being sent between data systems using different communication protocols and message structures described in U.S. patent application Ser. No. 13/421,776, entitled "Scalable Communication System," and filed on Mar. 15, 2012, the disclosure of which is hereby incorporated by reference in its entirety for all purposes. The memory 42 of the monitoring system 40 can include, for example, an interface module for communicating with the server 130. The interface module can include information on the communication protocol and data structure used by the server 130 and is configured to both receive messages from and transmit messages to the server 130.

In certain aspects where the medical entity is or otherwise includes a medical item, the history of the medical entity can include a number of times the medical item has been dispensed. For example, the history of the medical entity can indicate that the psychoactive drug alprazolam has been dispensed by a specific caregiver over ten times in the past twenty four hours. The first course of action associated with the medical item alprazolam may indicate an instruction to dispense alprazolam for a specific patient, and the second course of action can indicate an instruction to restrict dispensing of alprazolam (e.g., by locking the device 160 for dispensing alprazolam), for example, due to the specific caregiver's abnormally high rate of dispensing of alprazolam. A notification can be sent to the device 160 for dispensing alprazolam or the caregiver's mobile device 160 indicating that dispensing of alprazolam has been restricted based on the caregiver's abnormally high rate of dispensing of alprazolam. Alternatively, the alprazolam may be removed from the listing of available medications to the caregiver (e.g., "unprofiling" the medication) until a pharmacist or other authorized caregiver takes appropriate action, such as contacting the physician or repeating a lab test.

In certain other aspects where the medical entity is or otherwise includes a medical item, the processor 212 of the monitoring system 40 may be configured to receive a third identifier for a caregiver (e.g., from the medical entity database 62 over the network 30) in the institution. The history of the medical item can include a level of waste of the medical item by the caregiver. For example, the history of the medical item can indicate that it is an antihypertensive that is wasted (e.g., dispensed but never used) by the caregiver on average 22% of the times it is dispensed by the caregiver. The waste may occur due to, for example, resolution of the condition for which the medication was prescribed, patient-perceived ineffectiveness, prescription changes by the physician, and patient-perceived adverse effects. The abnormally high rate of wastage by the caregiver may be due to the caregiver being prone to not checking a patient's record before dispensing a medication. The first course of action associated with the antihypertensive medication may indicate an instruction to the caregiver to dispense a ten count of the antihypertensive medication, and the second course of action can indicate an instruction to decrease the dispensing count of the antihypertensive medication to two, or restrict dispensing altogether, for example, based on the caregivers history of wasting the antihypertensive medication. A notification can be sent to the device 160 for dispensing the antihypertensive medication or the caregiver's mobile device 160 indicating that dispensing of the antihypertensive medication has been reduced or restricted due to the caregiver's history of wasting the antihypertensive medication.

In certain further aspects where the medical entity is or otherwise includes a medical item, the history of the medical entity can include an average amount of time between dispensing of the medical item and the medical item being administered to a patient. For example, the average amount of time for dispensing a solution of adrenaline in an institution is 45 minutes, and a first course of action associated with the solution of adrenaline is to dispense the solution of adrenaline according to normal procedures. The second course of action associated with the dispensing solution can be to dispense the solution of adrenaline statim (e.g., according to expedited procedures) because adrenaline is commonly needed urgently to administer to a patient and an average wait time of 45 minutes for the solution is not acceptable. A notification can be sent to the pharmacy information system 36, nurse station 44, or other device 160 indicating the expedited need for the adrenaline solution.

In certain aspects where the medical entity is or otherwise includes a medical location, such as a ward in a hospital, the hospital itself, or a campus of multiple hospitals, the history of the medical location can include, for example, a rate of improvement of patients associated with the medical location. For example, the history of the medical location such as a pediatric intensive care unit (PICU) may indicate a sharp decline in immunity levels of patients in the PICU. The first course of action associated with the medical location may indicate an instruction to order a small amount of a macrolide antibiotic, azithromycin, to treat immunity deficiency in the PICU, and the second course of action can indicate an instruction to recommend an increase in the amount of azithromycin being ordered for the PICU, for example, due to the sharp decline in patient immunity levels. A notification can be sent to the pharmacy information system 36, nurse station 44, or other device 160 indicating the recommendation for the increased need for azithromycin.

In certain other aspects where the medical entity is or otherwise includes a medical location, the history of the medical entity can include an incidence rate of illness associated with the medical location. For example, the history of a specific hospital may indicate that the incidence of the influenza virus has dramatically increased over the past seven days from an average of three new influenza cases per day to over twenty influenza cases per day. The first course of action associated with the specific hospital may indicate an instruction to order a small amount of an antiviral drug, oseltamivir, to treat influenza, and the second course of action can indicate an instruction to increase the amount of oseltamivir being ordered for the specific hospital, for example, due to the sharp increase in daily incidence of influenza. A notification can be sent to the pharmacy information system 36, nurse station 44, or other device 160 indicating an increased need for oseltamivir.

In certain aspects, the processor 212 of the monitoring system 40 is configured to receive a first identity of a caregiver at an institution and a proposed course of action for a medical entity, generate, based on a history of the caregiver within the institution, a modified course of action, and provide a notification of the modified course of action to the caregiver. For example, the history of the caregiver can indicate a level of waste of a medical item by the caregiver, and the modified course of action can include an indication of an action to decrease a level of waste of the medical item by the caregiver. The indicated action can be, for example, an instruction to reduce the number of the medical items being dispensed. As another example, the history of the caregiver can include an identification of one or many error made by the caregiver with a medical item or patient, and the modified course of action can include an indication of an action to decrease a likelihood of the error with the medical item, the patient, another medical item, or another patient. The indicated action can be, for instance, an instruction to not perform a certain action with a patient or medical item, or a suggestion for additional training.

Figure 3:
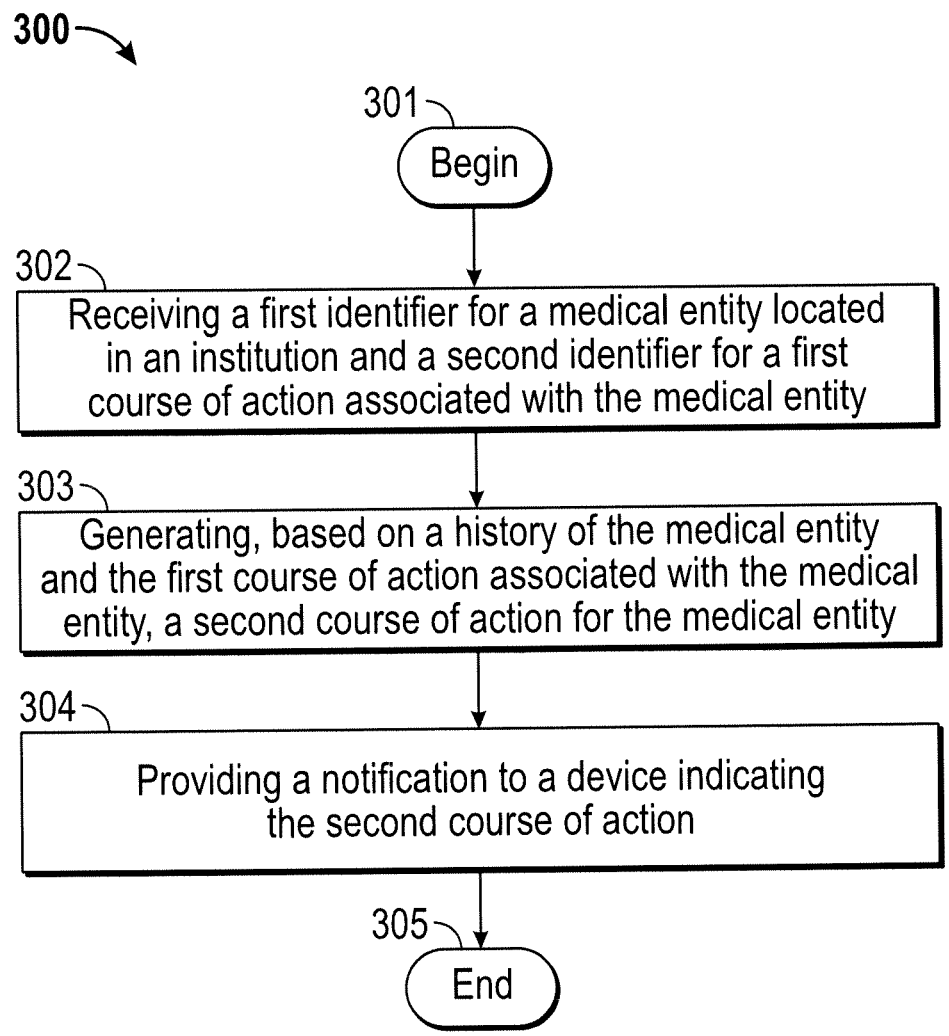
FIG. 3 illustrates an example process for facilitating safe use of a medical item using the example monitoring system of FIG. 2.

FIG. 3 illustrates an example process 300 for facilitating safe use of a medical item using the example monitoring system 40 of FIG. 2. While FIG. 3 is described with reference to FIG. 2, it should be noted that the process steps of FIG. 3 may be performed by other systems. The process 300 begins by proceeding from beginning step 301 when a request is initiated to perform an action associated with a medical entity, to step 302 when a first identifier for a medical entity located in an institution and a second identifier for a first course of action associated with the medical entity are received. The medical entity can include at least one of a patient, medical device, medical location, or medical item. Next, in step 303, a second course of action for the medical entity is generated based on a history of the medical entity and the first course of action associated with the medical entity. Finally, in step 304, a notification is provided to a device 160 indicating the second course of action. The process 300 then ends in step 305.

FIG. 3 set forth an example process 300 for facilitating safe use of a medical item using the example monitoring system 40 of FIG. 2. An example will now be described using the example process 300 of FIG. 3, a medical entity that is a medication, a device 160 that is an infusion pump (e.g., infusion pump 80), and an error-prone caregiver.

Figure 4:
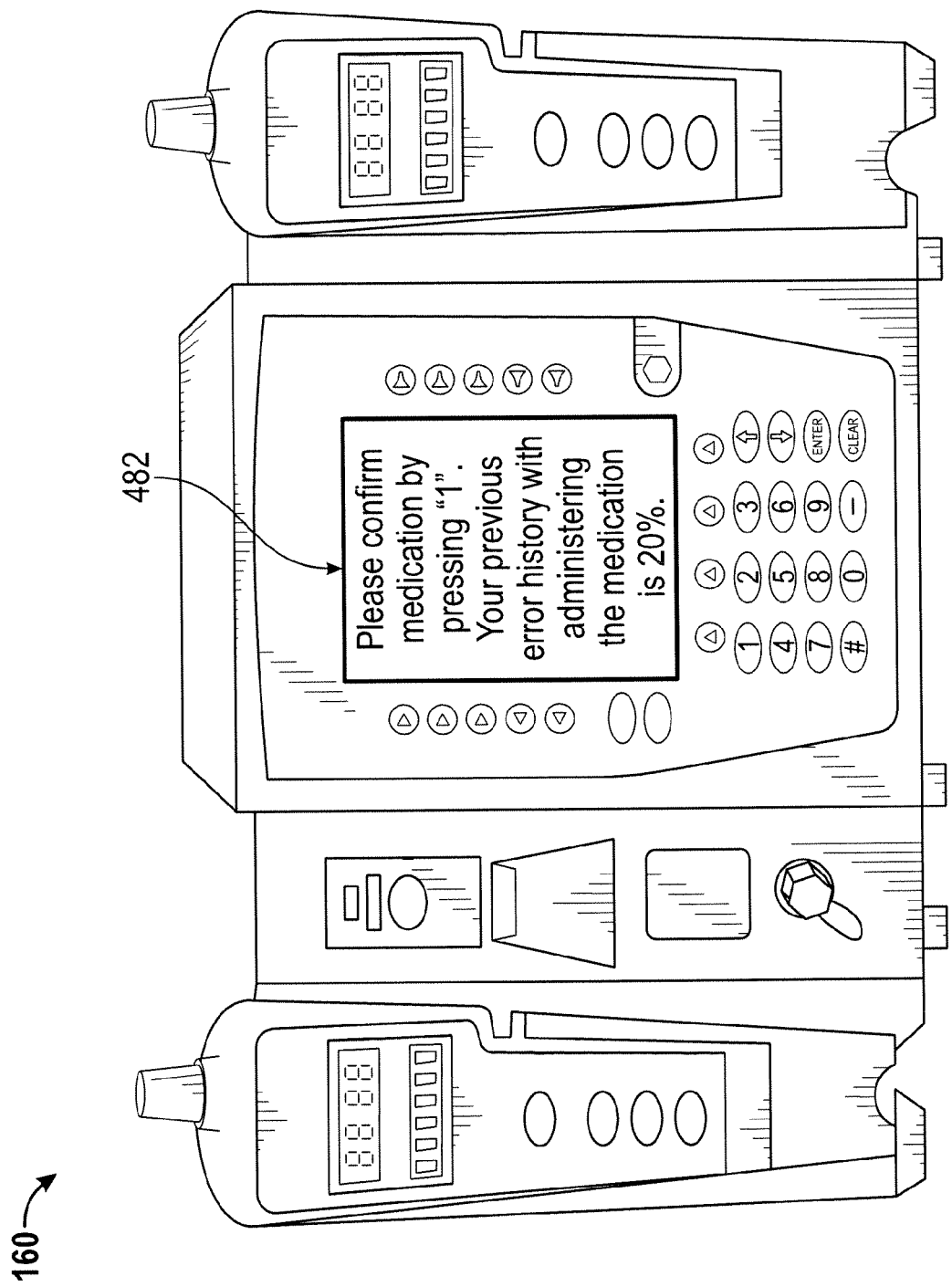
FIG. 4 is an example illustration of a medical item, namely a medical device, associated with the example process of FIG. 3.

The process 300 begins by proceeding from beginning step 301 when the caregiver enters parameters into the infusion pump 160 to administer a medication, to step 302 when a monitoring system 40 receives a first identifier identifying the medication and a second identifier identifying a first course of action, namely, certain parameters entered by the caregiver into the infusion pump 160 in order to administer the medication. Next, in step 303, a second course of action, namely, a requirement to confirm the medication parameters before administration, is generated based on a history of the medication and the entered parameters for administering the medication. Specifically, the history of the medication indicates that the caregiver has previously administered the medication incorrectly 20% of the time. Finally, as provided in the example illustration of FIG. 4, in step 304, a notification 482 requiring confirmation from the caregiver is provided for display on the infusion pump 160. The process 300 then ends in step 305.

Figure 5:
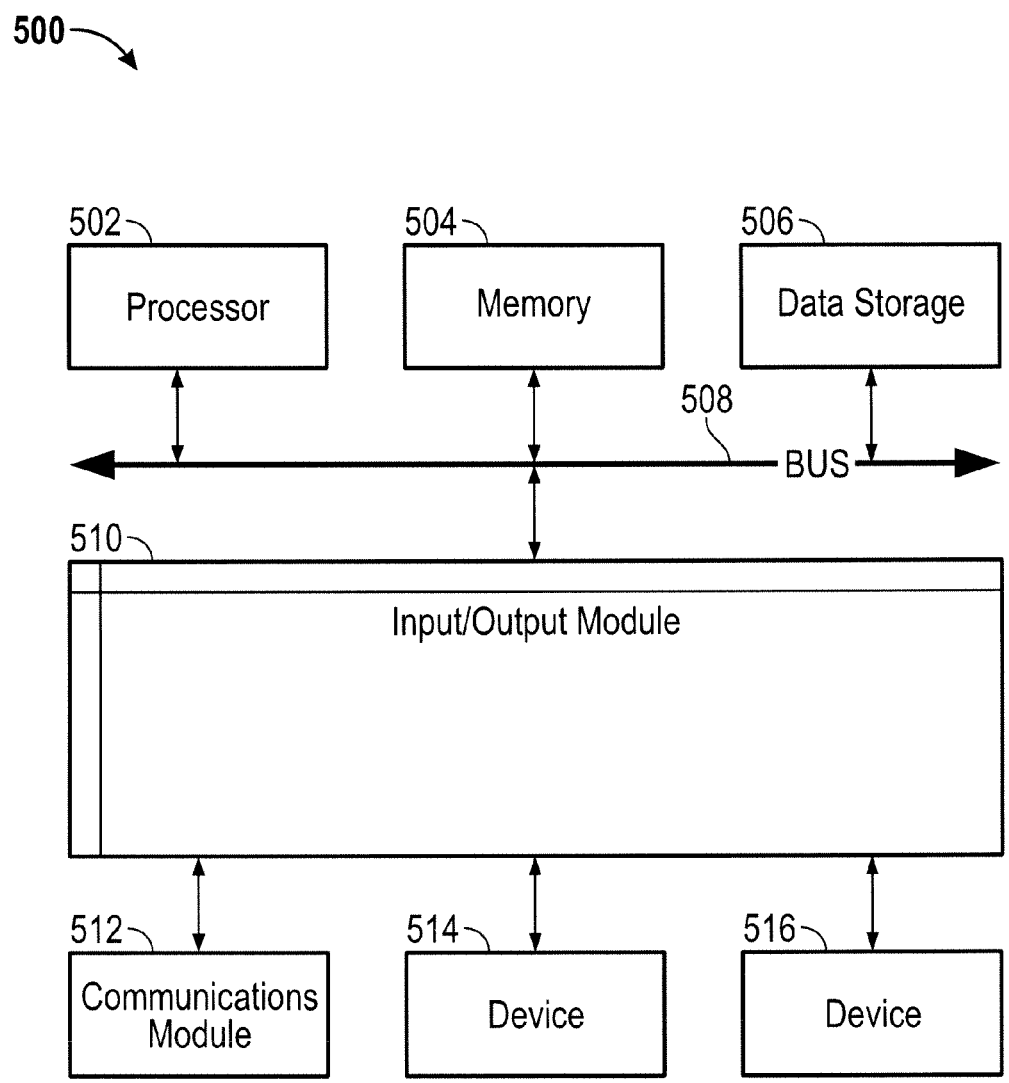
FIG. 5 is a block diagram illustrating an example computer system with which the clients and server of FIG. 2 can be implemented.

FIG. 5 is a block diagram illustrating an example computer system 500 with which the monitoring system 40, the device 160, and the server 130 of FIG. 2 can be implemented. In certain aspects, the computer system 500 may be implemented using hardware or a combination of software and hardware, either in a dedicated server, or integrated into another entity, or distributed across multiple entities.

Computer system 500 (e.g., monitoring system 40, the device 160, and the server 130) includes a bus 508 or other communication mechanism for communicating information, and a processor 502 (e.g., processor 212, 154, and 136) coupled with bus 508 for processing information. By way of example, the computer system 500 may be implemented with one or more processors 502. Processor 502 may be a general-purpose microprocessor, a microcontroller, a Digital Signal Processor (DSP), an Application Specific Integrated Circuit (ASIC), a Field Programmable Gate Array (FPGA), a Programmable Logic Device (PLD), a controller, a state machine, gated logic, discrete hardware components, or any other suitable entity that can perform calculations or other manipulations of information.

Computer system 500 can include, in addition to hardware, code that creates an execution environment for the computer program in question, e.g., code that constitutes processor firmware, a protocol stack, a database management system, an operating system, or a combination of one or more of them stored in an included memory 504 (e.g., memory 42, 152, or 132), such as a Random Access Memory (RAM), a flash memory, a Read Only Memory (ROM), a Programmable Read-Only Memory (PROM), an Erasable PROM (EPROM), registers, a hard disk, a removable disk, a CD-ROM, a DVD, or any other suitable storage device, coupled to bus 508 for storing information and instructions to be executed by processor 502. The processor 502 and the memory 504 can be supplemented by, or incorporated in, special purpose logic circuitry.

The instructions may be stored in the memory 504 and implemented in one or more computer program products, i.e., one or more modules of computer program instructions encoded on a computer readable medium for execution by, or to control the operation of, the computer system 500, and according to any method well known to those of skill in the art, including, but not limited to, computer languages such as data-oriented languages (e.g., SQL, dBase), system languages (e.g., C, Objective-C, C++, Assembly), architectural languages (e.g., Java, .NET), and application languages (e.g., PHP, Ruby, Perl, Python). Instructions may also be implemented in computer languages such as array languages, aspect-oriented languages, assembly languages, authoring languages, command line interface languages, compiled languages, concurrent languages, curly-bracket languages, dataflow languages, data-structured languages, declarative languages, esoteric languages, extension languages, fourth-generation languages, functional languages, interactive mode languages, interpreted languages, iterative languages, list-based languages, little languages, logic-based languages, machine languages, macro languages, metaprogramming languages, multiparadigm languages, numerical analysis, non-English-based languages, object-oriented class-based languages, object-oriented prototype-based languages, off-side rule languages, procedural languages, reflective languages, rule-based languages, scripting languages, stack-based languages, synchronous languages, syntax handling languages, visual languages, wirth languages, embeddable languages, and xml-based languages. Memory 504 may also be used for storing temporary variable or other intermediate information during execution of instructions to be executed by processor 502.

A computer program as discussed herein does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, subprograms, or portions of code). A computer program can be deployed to be executed on one computer or on multiple computers that are located at one site or distributed across multiple sites and interconnected by a communication network. The processes and logic flows described in this specification can be performed by one or more programmable processors executing one or more computer programs to perform functions by operating on input data and generating output.

Computer system 500 further includes a data storage device 506 such as a magnetic disk or optical disk, coupled to bus 508 for storing information and instructions. Computer system 500 may be coupled via input/output module 510 to various devices. The input/output module 510 can be any input/output module. Example input/output modules 510 include data ports such as USB ports. The input/output module 510 is configured to connect to a communications module 512. Example communications modules 512 (e.g., communications module 210, 156, and 138) include networking interface cards, such as Ethernet cards and modems. In certain aspects, the input/output module 510 is configured to connect to a plurality of devices, such as an input device 514 (e.g., input device 216) and/or an output device 516 (e.g., display device 214). Example input devices 514 include a keyboard and a pointing device, e.g., a mouse or a trackball, by which a user can provide input to the computer system 500. Other kinds of input devices 514 can be used to provide for interaction with a user as well, such as a tactile input device, visual input device, audio input device, or brain-computer interface device. For example, feedback provided to the user can be any form of sensory feedback, e.g., visual feedback, auditory feedback, or tactile feedback; and input from the user can be received in any form, including acoustic, speech, tactile, or brain wave input. Example output devices 516 include display devices, such as a LED (light emitting diode), CRT (cathode ray tube), or LCD (liquid crystal display) screen, for displaying information to the user.

According to one aspect of the present disclosure, the monitoring system 40, the device 160, and the server 130 can be implemented using a computer system 500 in response to processor 502 executing one or more sequences of one or more instructions contained in memory 504. Such instructions may be read into memory 504 from another machine-readable medium, such as data storage device 506. Execution of the sequences of instructions contained in main memory 504 causes processor 502 to perform the process steps described herein. One or more processors in a multi-processing arrangement may also be employed to execute the sequences of instructions contained in memory 504. In alternative aspects, hard-wired circuitry may be used in place of or in combination with software instructions to implement various aspects of the present disclosure. Thus, aspects of the present disclosure are not limited to any specific combination of hardware circuitry and software.

Various aspects of the subject matter described in this specification can be implemented in a computing system that includes a back end component, e.g., as a data server, or that includes a middleware component, e.g., an application server, or that includes a front end component, e.g., a client computer having a graphical user interface or a Web browser through which a user can interact with an implementation of the subject matter described in this specification, or any combination of one or more such back end, middleware, or front end components. The components of the system can be interconnected by any form or medium of digital data communication, e.g., a communication network. The communication network (e.g., network 30) can include, for example, any one or more of a personal area network (PAN), a local area network (LAN), a campus area network (CAN), a metropolitan area network (MAN), a wide area network (WAN), a broadband network (BBN), the Internet, and the like. Further, the communication network can include, but is not limited to, for example, any one or more of the following network topologies, including a bus network, a star network, a ring network, a mesh network, a star-bus network, tree or hierarchical network, or the like. The communications modules can be, for example, modems or Ethernet cards.

Computing system 500 can include clients and servers. A client and server are generally remote from each other and typically interact through a communication network. The relationship of client and server arises by virtue of computer programs running on the respective computers and having a client-server relationship to each other. Computer system 500 can be, for example, and without limitation, a desktop computer, laptop computer, or tablet computer. Computer system 500 can also be embedded in another device, for example, and without limitation, a mobile telephone, a personal digital assistant (PDA), a mobile audio player, a Global Positioning System (GPS) receiver, a video game console, and/or a television set top box.

The term "machine-readable storage medium" or "computer readable medium" as used herein refers to any medium or media that participates in providing instructions or data to processor 502 for execution. Such a medium may take many forms, including, but not limited to, non-volatile media, volatile media, and transmission media. Non-volatile media include, for example, optical disks, magnetic disks, or flash memory, such as data storage device 506. Volatile media include dynamic memory, such as memory 504. Transmission media include coaxial cables, copper wire, and fiber optics, including the wires that comprise bus 508. Common forms of machine-readable media include, for example, floppy disk, a flexible disk, hard disk, magnetic tape, any other magnetic medium, a CD-ROM, DVD, any other optical medium, punch cards, paper tape, any other physical medium with patterns of holes, a RAM, a PROM, an EPROM, a FLASH EPROM, any other memory chip or cartridge, or any other medium from which a computer can read. The machine-readable storage medium can be a machine-readable storage device, a machine-readable storage substrate, a memory device, a composition of matter effecting a machine-readable propagated signal, or a combination of one or more of them.

As used herein, the phrase "at least one of" preceding a series of items, with the terms "and" or "or" to separate any of the items, modifies the list as a whole, rather than each member of the list (i.e., each item). The phrase "at least one of" does not require selection of at least one item; rather, the phrase allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

Furthermore, to the extent that the term "include," "have," or the like is used in the description or the claims, such term is intended to be inclusive in a manner similar to the term "comprise" as "comprise" is interpreted when employed as a transitional word in a claim.

A reference to an element in the singular is not intended to mean "one and only one" unless specifically stated, but rather "one or more." The term "some" refers to one or more. All structural and functional equivalents to the elements of the various configurations described throughout this disclosure that are known or later come to be known to those of ordinary skill in the art are expressly incorporated herein by reference and intended to be encompassed by the subject technology. Moreover, nothing disclosed herein is intended to be dedicated to the public regardless of whether such disclosure is explicitly recited in the above description.

While this specification contains many specifics, these should not be construed as limitations on the scope of what may be claimed, but rather as descriptions of particular implementations of the subject matter. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the aspects described above should not be understood as requiring such separation in all aspects, and it should be understood that the described program components and systems can generally be integrated together in a single software product or packaged into multiple software products.

The subject matter of this specification has been described in terms of particular aspects, but other aspects can be implemented and are within the scope of the following claims. For example, the actions recited in the claims can be performed in a different order and still achieve desirable results. As one example, the processes depicted in the accompanying figures do not necessarily require the particular order shown, or sequential order, to achieve desirable results. In certain implementations, multitasking and parallel processing may be advantageous. Other variations are within the scope of the following claims.

These and other implementations are within the scope of the following claims.

What is claimed is:

1. A method, comprising:
    receiving, by a monitoring system, a first identifier for a medication, a second identifier for a first course of action for administering the medication with an infusion pump, and a third identifier for a caregiver;
    obtaining, by a processor of the monitoring system, medication orders from a medical entity database;
    reviewing, by the processor, the medication orders based on the received identifiers;
    determining, by the processor, the caregiver's level of waste for the medication based on a history of the medication being dispensed but never used by the caregiver;
    generating, by the processor, a second course of action based on the caregiver's level of waste for the medication order to be dispensed;
    providing, by the processor via a communications module of the monitoring system, instructions to the infusion pump prior to implementation of the first course of action, wherein the instructions comprise instructions for the infusion pump to take the second course of action in place of the first course of action; and
    performing, by the infusion pump responsive to the instructions, the second course of action by (a) restricting operation of the infusion pump to perform the first course of action until appropriate authorization for performing the first course of action is received by the infusion pump from the caregiver, and (b) providing, with the infusion pump to the caregiver, a notification including a purpose for taking the second course of action based on the caregiver's history of wasting the medication.

2. The method of claim 1, wherein the at least one of the first identifier, the second identifier, or the history of the medical entity is received over a network from a healthcare facility information system in a native message format of the healthcare facility information system and converted into an internal messaging format configured for use with the monitoring system.

3. The method of claim 1, wherein the first course of action comprises a plurality of parameters for administration of the medication by the infusion pump.

4. The method of claim 1, wherein the purpose comprises a level of waste of the medication by the caregiver.

5. A non-transitory machine-readable storage medium comprising machine-readable instructions for causing a processor of a monitoring system in communication with an infusion pump to execute a method, the method comprising:
    receiving, at a monitoring system, a first identifier for a medication, a second identifier for a first course of action for administering the medication with an infusion pump, and a third identifier for a caregiver;
    obtaining, by a processor of the monitoring system, medication orders from a medical entity database;
    reviewing, by the processor, the medication orders based on the received identifiers;
    determining, by the processor, the caregiver's level of waste for the medication based on a history of the medication being dispensed but never used by the caregiver;
    generating, by the processor, a second course of action based on the caregiver's level of waste for the medication order to be dispensed;
    providing, by the processor via a communications module of the monitoring system, instructions to the infusion pump prior to implementation of the first course of action, wherein the instructions comprise instructions for the infusion pump to take the second course of action in place of the first course of action,
    wherein the second course of action comprises (a) restricting operation of the infusion pump for performance of the first course of action until appropriate authorization for performing the first course of action is received at the infusion pump by the caregiver, and (b) providing, with the infusion pump to the caregiver, a notification including a purpose for taking the second course of action based on the caregiver's history of wasting the medication.

6. The non-transitory machine-readable storage medium of claim 5, wherein the at least one of the first identifier, the second identifier, or the history of the medical entity is received over a network from a healthcare facility information system in a native message format of the healthcare facility information system and converted into an internal messaging format configured for use with the monitoring system.

7. The non-transitory machine-readable storage medium of claim 5, wherein the first course of action comprises a plurality of parameters for administration of the medication by the infusion pump.

8. The non-transitory machine-readable storage medium of claim 5, wherein the purpose comprises a level of waste of the medication by the caregiver.

* * * * *